United States Patent
Turner et al.

(10) Patent No.: US 10,480,027 B2
(45) Date of Patent: Nov. 19, 2019

(54) NANOPORE SEQUENCING METHODS

(71) Applicant: Pacific Biosciences of California, Inc., Menlo Park, CA (US)

(72) Inventors: Stephen Turner, Eugene, OR (US); Jonas Korlach, Camas, WA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 106 days.

(21) Appl. No.: 15/869,416

(22) Filed: Jan. 12, 2018

(65) Prior Publication Data
US 2018/0201993 A1    Jul. 19, 2018

Related U.S. Application Data

(63) Continuation of application No. 14/831,599, filed on Aug. 20, 2015, now abandoned, which is a (Continued)

(51) Int. Cl.
  *C12Q 1/6869* (2018.01)
  *C12Q 1/68* (2018.01)
  (Continued)

(52) U.S. Cl.
  CPC ............ *C12Q 1/6869* (2013.01); *C12Q 1/68* (2013.01); *C12Q 1/6874* (2013.01); *G01N 27/447* (2013.01); *G01N 33/48721* (2013.01)

(58) Field of Classification Search
  CPC ............ C12Q 1/6869; C12Q 2521/543; C12Q 2565/631; C12Q 1/68; C12Q 33/48721
  See application file for complete search history.

(56) References Cited

U.S. PATENT DOCUMENTS

| 5,001,050 A | 5/1991 | Blanco et al. |
| 5,409,811 A | 4/1995 | Tabor et al. |
| (Continued) | | |

FOREIGN PATENT DOCUMENTS

| EP | 1963530 B1 | 7/2011 |
| WO | 2002086088 A2 | 10/2002 |
| (Continued) | | |

OTHER PUBLICATIONS

Combined Search & Exam Report dated May 18, 2018 for related GB 1807346.0.
(Continued)

*Primary Examiner* — Teresa E Strzelecka
(74) *Attorney, Agent, or Firm* — Robert H. Reamey

(57) ABSTRACT

Methods are provided for sequencing of nucleic acid templates using nanopores. A polymerase-nucleic acid complex having a strand displacing polymerase is provided. The nucleic acid in the polymerase-nucleic acid complex is a circular nucleic acid template. Components required for nucleic acid synthesis are provided whereby the polymerase produces a nascent strand that passes through the nanopore while the nascent strand is produced. Current through the nanopore over time is measured allowing for the determination of the sequence of the nascent strand as it translates through the pore using the measured current over time. Because the polymerase can proceed around the circular template multiple times, multiple reads corresponding to the same sequence in the circular template can be obtained in one sequencing process. Where modified bases are present in the template, the method can be used to determine the presence and position of the modified bases using the kinetics of the polymerase.

20 Claims, 14 Drawing Sheets

Related U.S. Application Data continuation of application No. 14/618,311, filed on Feb. 10, 2015, now Pat. No. 9,150,918, which is a continuation of application No. 13/914,361, filed on Jun. 10, 2013, now Pat. No. 9,116,118.

(60) Provisional application No. 61/657,583, filed on Jun. 8, 2012.

(51) Int. Cl.
*C12Q 1/6874* (2018.01)
*G01N 27/447* (2006.01)
*G01N 33/487* (2006.01)

(56) References Cited

U.S. PATENT DOCUMENTS

| | | |
|---|---|---|
| 6,165,765 A | 12/2000 | Hong et al. |
| 6,399,320 B1 | 6/2002 | Markau et al. |
| 6,399,335 B1 | 6/2002 | Kao et al. |
| 6,447,724 B1 | 9/2002 | Jensen et al. |
| 6,610,486 B1 | 8/2003 | Dahlhauser |
| 6,762,048 B2 | 7/2004 | Williams et al. |
| 6,787,308 B2 | 9/2004 | Balasubramanian et al. |
| 6,936,702 B2 | 6/2005 | Williams et al. |
| 6,917,726 B2 | 7/2005 | Levene et al. |
| 7,041,812 B2 | 5/2006 | Kumar et al. |
| 7,056,661 B2 | 6/2006 | Korlach et al. |
| 7,057,026 B2 | 6/2006 | Barnes et al. |
| 7,315,019 B2 | 1/2008 | Turner et al. |
| 7,901,889 B2 | 3/2011 | Christians et al. |
| 7,972,858 B2 | 7/2011 | Meller et al. |
| 8,003,330 B2 | 8/2011 | Henier et al. |
| 8,133,672 B2 | 3/2012 | Bjornson et al. |
| 8,153,375 B2 | 4/2012 | Travers et al. |
| 8,530,164 B2 | 9/2013 | Patel et al. |
| 8,852,864 B2 | 10/2014 | Cantor |
| 9,017,937 B1 | 4/2015 | Turner et al. |
| 2002/0197618 A1 | 12/2002 | Sampson |
| 2004/0033492 A1 | 2/2004 | Chen |
| 2006/0003458 A1 | 1/2006 | Golovchenko et al. |
| 2006/0019247 A1 | 1/2006 | Su et al. |
| 2006/0051807 A1 | 3/2006 | Fuller |
| 2006/0063173 A1 | 3/2006 | Williams et al. |
| 2007/0036511 A1 | 2/2007 | Lundquist et al. |
| 2007/0077564 A1 | 4/2007 | Roitman et al. |
| 2007/0188750 A1 | 8/2007 | Lundquist et al. |
| 2007/0196846 A1 | 8/2007 | Henzel et al. |
| 2007/0206187 A1 | 9/2007 | Lundquist et al. |
| 2008/0030628 A1 | 2/2008 | Lundquist et al. |
| 2008/0108082 A1 | 5/2008 | Rank et al. |
| 2008/0212960 A1 | 9/2008 | Lundquist et al. |
| 2008/0299565 A1 | 12/2008 | Schneider et al. |
| 2009/0029385 A1 | 1/2009 | Christians et al. |
| 2009/0118129 A1 | 5/2009 | Turner |
| 2009/0136958 A1 | 5/2009 | Gershow et al. |
| 2009/0280538 A1 | 11/2009 | Patel et al. |
| 2010/0047802 A1 | 2/2010 | Bjornson et al. |
| 2010/0075332 A1 | 3/2010 | Patel et al. |
| 2010/0112645 A1 | 5/2010 | Clark et al. |
| 2010/0143900 A1 | 6/2010 | Peluso et al. |
| 2010/0148126 A1 | 6/2010 | Guan et al. |
| 2010/0221716 A1 | 9/2010 | Flusberg et al. |
| 2010/0292101 A1 | 11/2010 | So |
| 2010/0330570 A1 | 12/2010 | Vander Horn et al. |
| 2010/0331194 A1 | 12/2010 | Turner et al. |
| 2011/0174625 A1 | 7/2011 | Akeson et al. |
| 2011/0183320 A1 | 7/2011 | Flusberg et al. |
| 2011/0244447 A1 | 10/2011 | Korlach |
| 2012/0094332 A1 | 4/2012 | Lee et al. |
| 2012/0160687 A1 | 6/2012 | Akeson et al. |
| 2012/0196279 A1 | 8/2012 | Underwood et al. |
| 2012/0322666 A1 | 12/2012 | Pham et al. |
| 2013/0165328 A1 | 6/2013 | Previte et al. |
| 2013/0303385 A1 | 11/2013 | Korlach et al. |
| 2014/0051068 A1 | 2/2014 | Cherf et al. |
| 2015/0152492 A1 | 6/2015 | Brown et al. |
| 2015/0247183 A1 | 9/2015 | Turner et al. |

FOREIGN PATENT DOCUMENTS

| | | |
|---|---|---|
| WO | 2007075987 A2 | 7/2007 |
| WO | 2007076057 A2 | 7/2007 |
| WO | 2007123763 A2 | 11/2007 |
| WO | 2007137060 A2 | 11/2007 |
| WO | 2008051530 A2 | 5/2008 |
| WO | 2008154317 A1 | 12/2008 |
| WO | 2009102470 A2 | 8/2009 |
| WO | 2009145828 A2 | 12/2009 |
| WO | 2010086622 A1 | 8/2010 |
| WO | 2012033524 A2 | 3/2012 |
| WO | 2015124935 A1 | 8/2015 |
| WO | 2016059363 A1 | 4/2016 |
| WO | 2016059436 A1 | 4/2016 |

OTHER PUBLICATIONS

Second Examination Report dated Jan. 19, 2018 for related GB 1500009.4.

Third Examination Report dated Mar. 27, 2018 for related GB 1500009.4.

Combined Search & Exam Report dated Mar. 29, 2018 for related GB 1803482.7.

Arndt et al. "Insight into the catalytic mechanism of DNA polymerase Beta: Structures of intermediate complexes" Biochem (2001) 40:5368-5375.

Arnold, J.J. et al. "Polivirus RNA-dependent RNA polymerase(3pol): pre-steady-state kinetic analysis of ribonucleotide incorporation in the presence of Mn2+" Biochem (2004) 43(18):5138-5148.

Ayub, et al., "Individual RNA Base Recognition in Immobilized Oligonucleotides Using a Protein Nanopore," NANO Letters (2012) 12:5637-5643.

Bakhtina et al. "Use of viscogens dNTPaS, and Rhodium (III) as probes in stopped-flow experiments to obtain new evidence for the mechanism of catalysis by DNA polymerase" Biochem (2005) 44(13):5177-5187.

Benner et al. "Sequence-Specific Detection of Individual DNA Polymerase Complexes in Real Time Using a Nanopore," Nature Nanotechnology 2 (2007) 718-724.

Berman et al. "Structures of phi29 polymerase complexes with substrate: the mechanism of translocation in polymerases" EMBO J (2007) 26:3494-3505.

Blanco et al. "Mutational analysis of bacteriophage phi29 DNA polymerase" Meth in Enzym (1995) 262:283-294.

Blasco et al. "phi29 DNA polymerase active site" J Biol Chem (1993) 268(22):16763-16770.

Castro et al. "Two proton transfers in the transition state for nucleotidyl transfer catalyzed by RNA and DNA-dependent RNA and DNA polymerases" PNAS (2007) 104(11):4267-4272.

Cherf et al. "Automated Forward and Reverse Ratcheting of DNA in a Nanopore at 5-Å Precision," Nat Biotechnol (2012) 30(4):344-8.

Cockroft et al. "A Single-Molecule Nanopore Device Detects DNA Polymerase Activity with Single-Nucleotide Resolution," J Am Chem Soc. (2008) 130(3):818-20.

Dahl et al. "Direct Observation of Translocation in Individual DNA Polymerase Complexes," J Biol Chem (2012) 287(16):13407-21.

Eid et al., "Real-Time DNA Sequencing From Single Polymerase Molecules," Science (2009) 323:133-138.

Esteban, J. A., et al., Biochemistry (1992) 31:350-359.

Garaj, et al., "Super-Sensitive Molecule-Hugging Graphene Nanopores," submitted on Apr. 19, 2012 (v1), last revised on May 17, 2012 (v2).

Korlach et al., "Long, Processive Enzymatic DNA Synthesis Using 100% Dye-Labeled Terminal Phosphate-Linked Nucleotides" Nucleosides, and Nucleotides and Nucleic Acids (2008) 27:1072-1083.

(56) References Cited

OTHER PUBLICATIONS

Korlach et al., "Selective aluminum passivation for targeted immobilization of single DNA polymerase molecules in zero-mode waveguide structures" PNAS (2008) 105(4):1176-1181.

Levene et al., "Zero-mode Waveguides for Single-molecule Analysis at High Concentration" Science (2003) 299:682-686.

Lieberman et al. "Processive Replication of Single DNA Molecules in a Nanopore Catalyzed by Phi29 DNA Polymerase," J Am Chem Soc. (2010) 132(5):17961-72.

Lundquist et al. "Parallel confocal detection of single molecules in real time" Opt Lett (2008) 33(9):1026-1028.

Manrao et al. "Reading DNA at Single-Nucleotide Resolution with a Mutant MspA Nanopore and Phi29 DNA Polymerase," Nature Biotechnology (2012) 30:349-353.

Miyake, T. et al., "Real-Time Imaging of Single-Molecule Fluorescence with a Zero-Mode Waveguide for the Analysis of Protein-Protein Interaction" Anal Chem (2008) 80:6018-6022.

Nicholson et al. "Enhanced protein thermostability from designed mutations that interact with alpha-helix dipoles" Nature (1988) 336:651-656.

Olasagasti et al. "Replication of Individual DNA Molecules Under Electronic Control Using a Protein Nanopore," Nature Nanotechnology 5 (2010) 798-806.

Rechkunova, N.I. et al. "Thermostable DNA polymerase from Thermus thermophilus B35: influence of divalent metal ions on the interaction with deoxynucleoside triphosphates" Biochem (2000) 65(5):609-614.

Shim et al., "Detection and Qualification of Methylation in DNA Using Solid-State Nanopores," Scientific Reports (2013) 3:1389, DOI:10.1038/rsrep01389.

Slatko, B. E., et al., "DNA Sequencing by the Dideoxy Method," Current Prot. Mol. Biol., Suppl. (1999) 47:7.4.A.1-7.4.A.39.

Soengas et al. "Site directed mutaenesis at the Exo III motif of phi29 DNA polymerase. Overlappying structural domains for the 3'-5' exonuclease and strand-displacement activities" EMBO J (1992) 11:4227-4237.

Tang et al. "Mismatched dNTP incorporation by DNA polymerase beta does not proceed via globally different conformational pathways" Nucl Acids Res (2008) 36(9):2948-2957.

Tock, M.R. et al. "Dynamic evidence for metal ion catalysis in the reaction mediated by a flap endonuclease" EMBO J. (2003) 22(5):995-1004.

Truniger et al. "A positively charged residue of phi29 DNA polymerase, highly conserved in DNA polymerases from families A and B, is involved in binding the incoming nucleotide" Nuc Acids Res (2002) 30(7):1483-1494.

Wilson et al. "Electronic Control of DNA Polymerase Binding and Unbinding to Single DNA Molecules," ACS Nano (2009) 3(4):995-1003.

Xie, S. et al. "Single-molecule enzymology" J Biol Chem (1999) 274(23):15967-15970.

Zhou et al. "Kinetic analysis of sequential multistep reactions" J Phys Chem B (2007) 111:13600-13610.

International Search Report and Written Opinion dated Oct. 8, 2013 for related PCT/US2013/045009.

International Preliminary Report on Patentability dated Dec. 18, 2014 for related PCT/US2013/045009.

First Examination Report dated Apr. 5, 2017 for related GB 1500009.4.

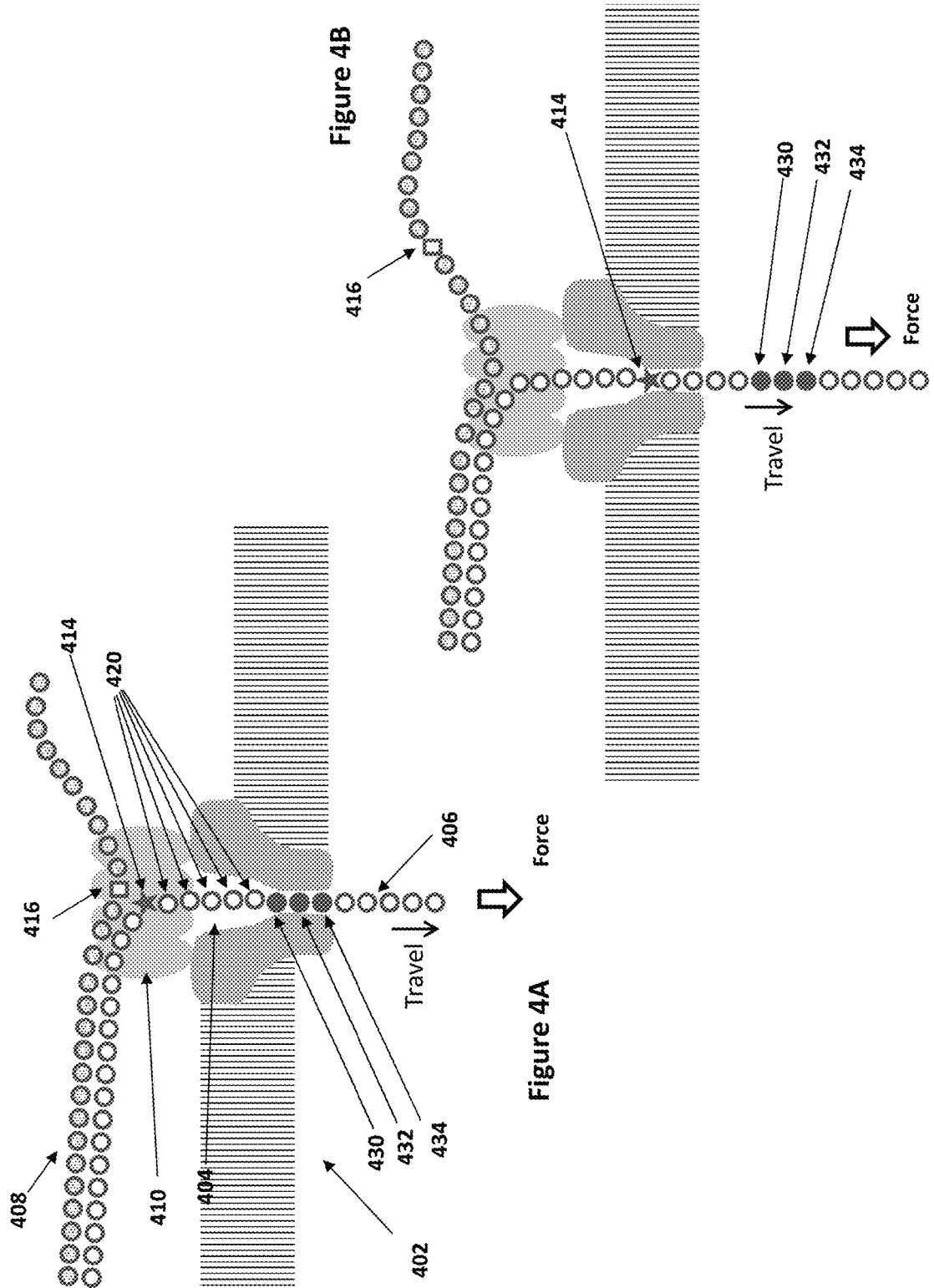

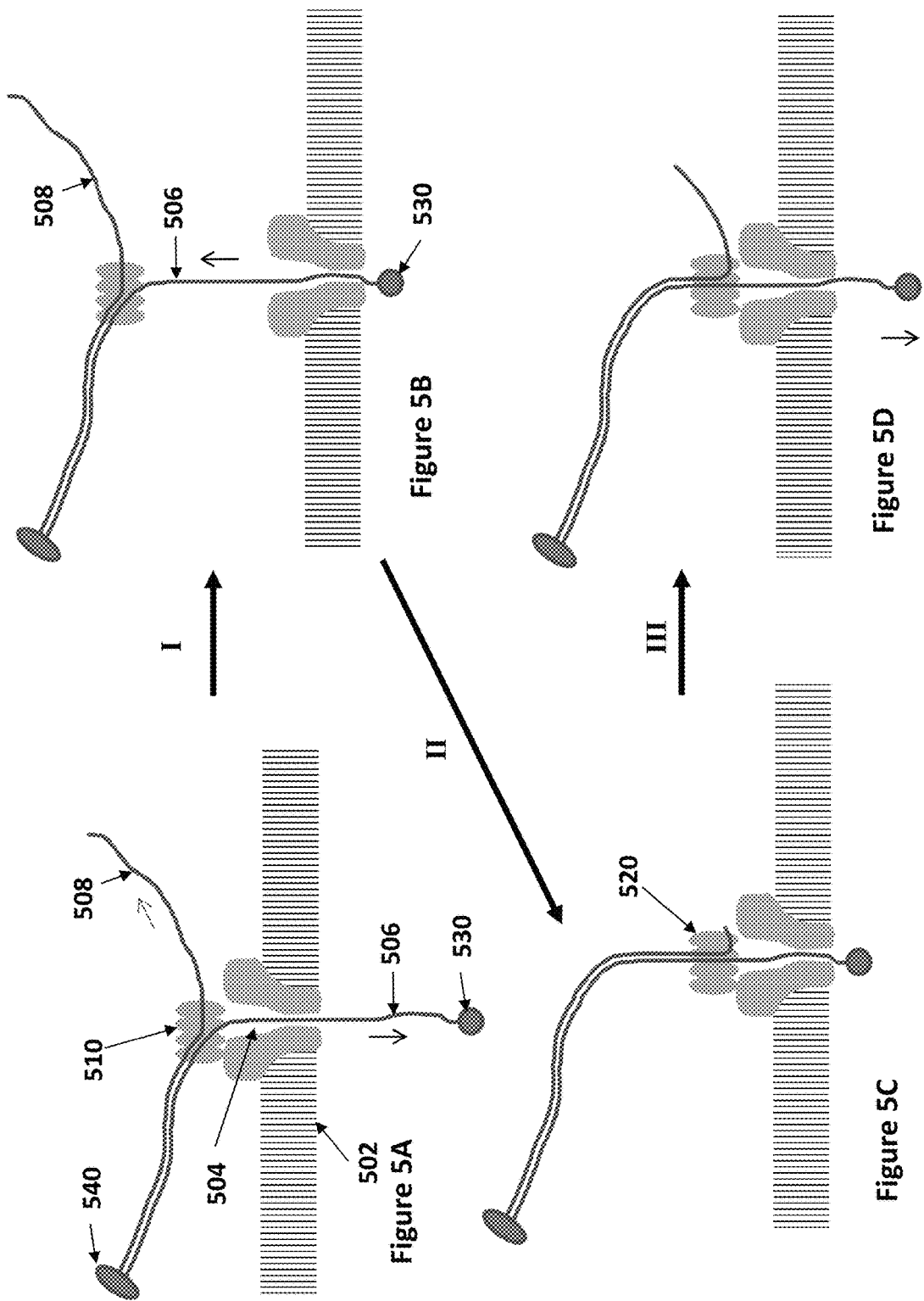

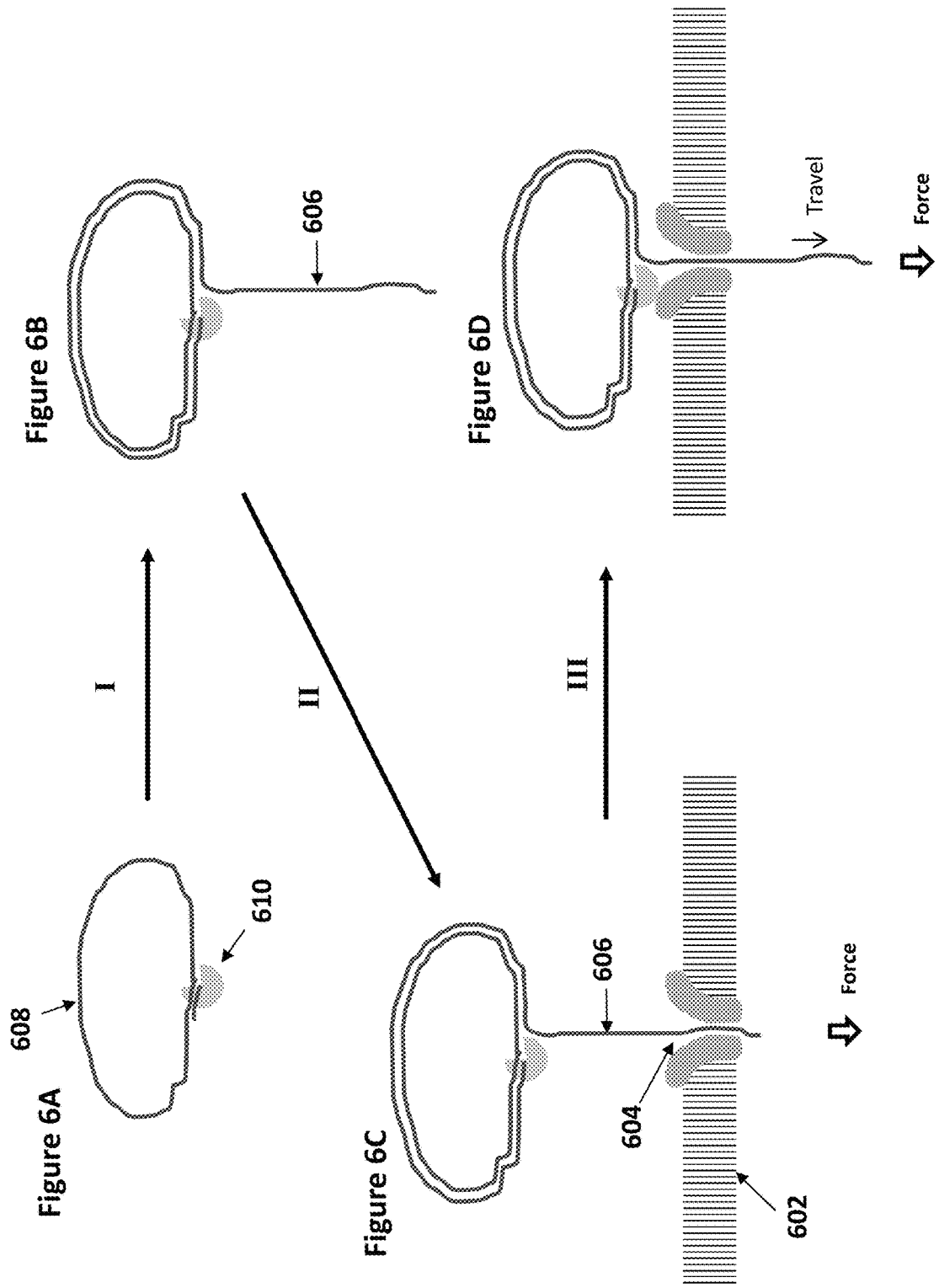

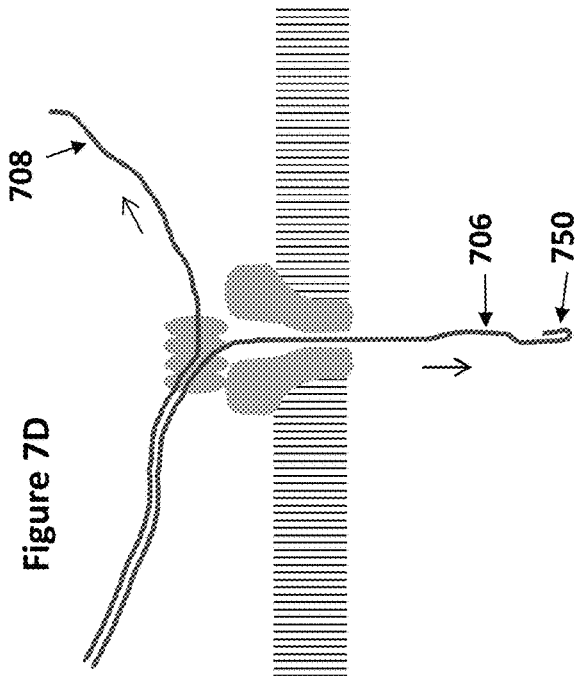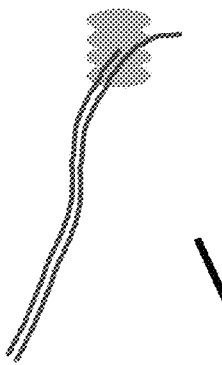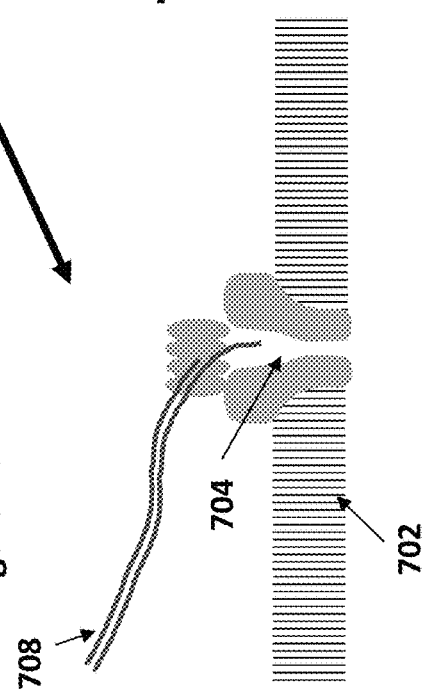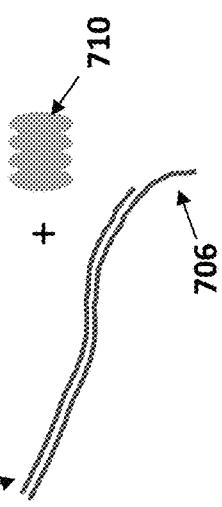

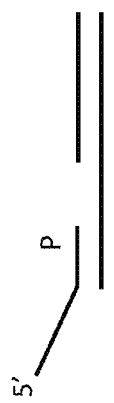
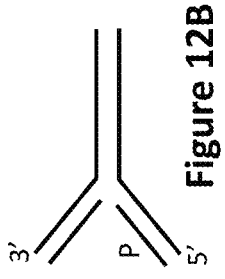
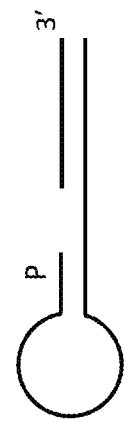
Figure 12A
Figure 12B
Figure 12C
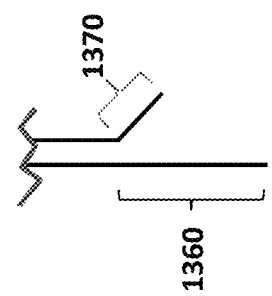
Figure 13

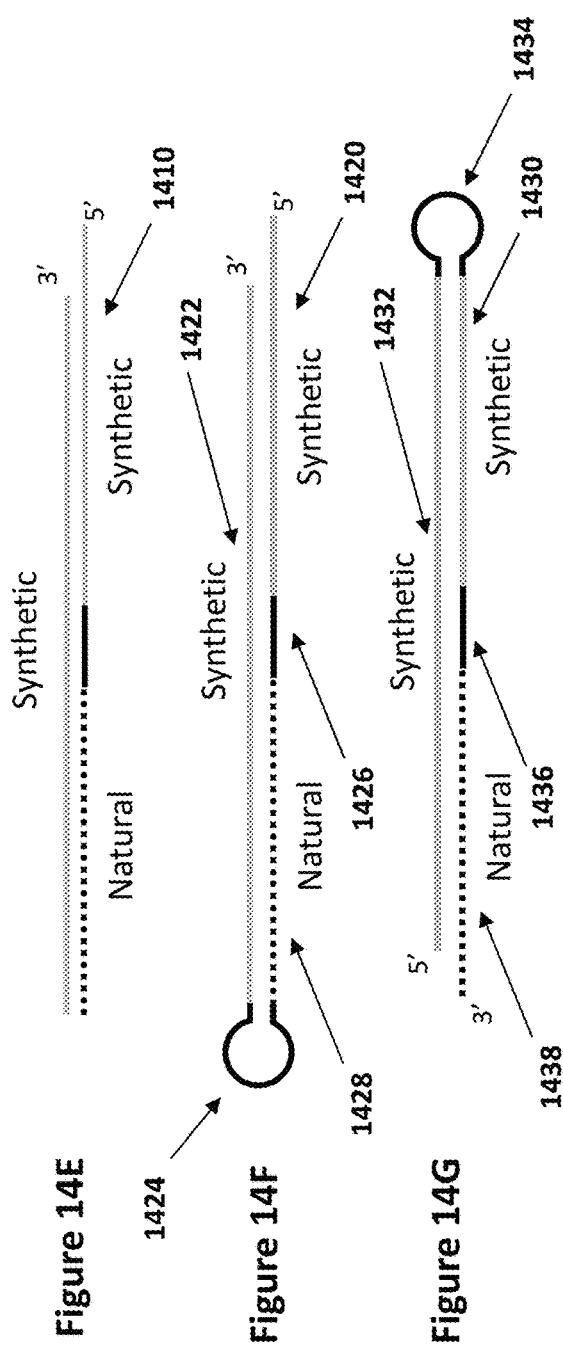

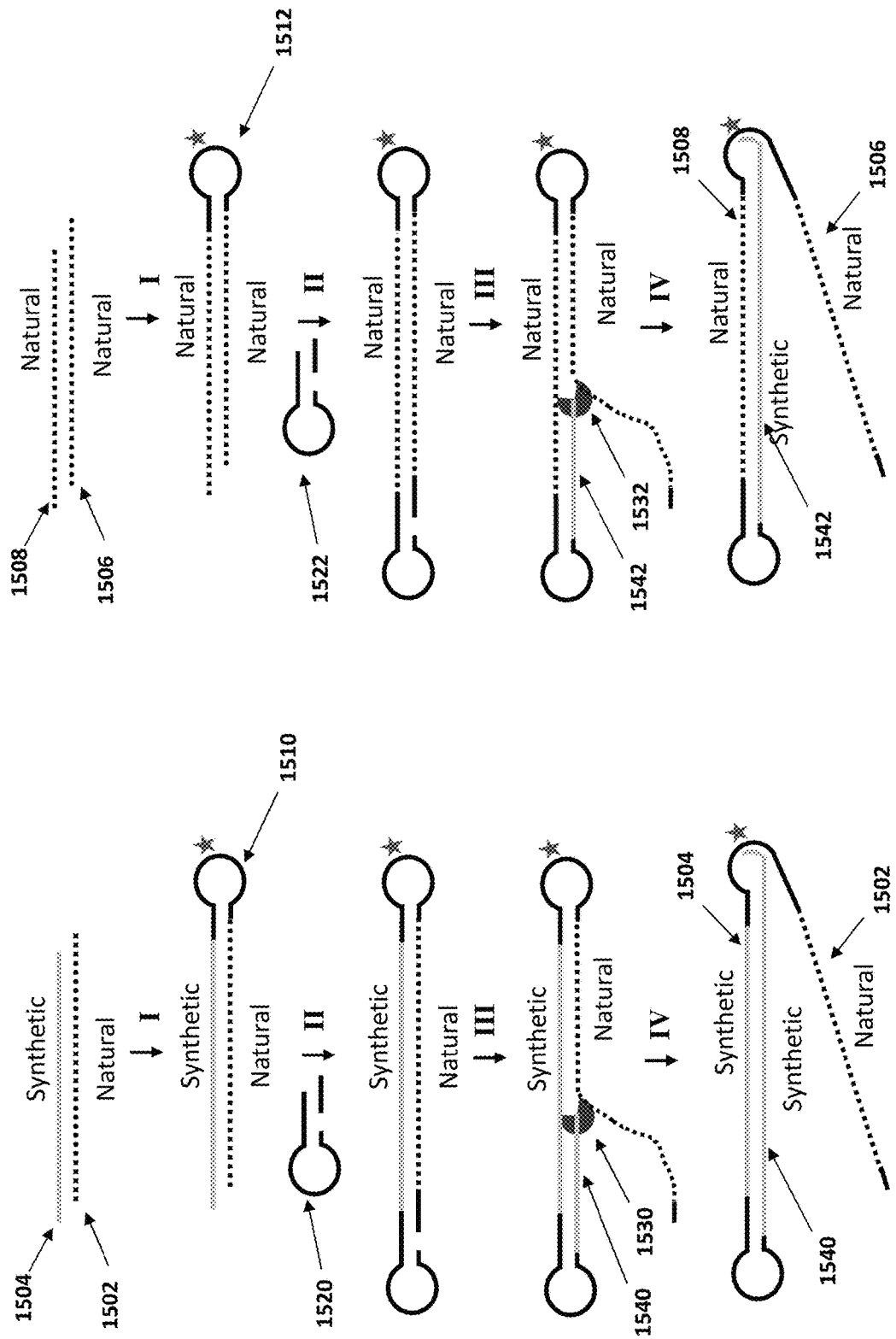

NANOPORE SEQUENCING METHODS

CROSS-REFERENCE TO RELATED APPLICATIONS

This application is a continuation of U.S. patent application Ser. No. 14/831,599, filed Aug. 20, 2015, which is a continuation of U.S. patent application Ser. No. 14/618,311, filed Feb. 10, 2015, which is a continuation application of U.S. patent application Ser. No. 13/914,361, filed Jun. 10, 2013, which claims the benefit of Provisional U.S. Patent Application No. 61/657,583, filed Jun. 8, 2012, the full disclosures of which are incorporated herein by reference in its entirety for all purposes.

BACKGROUND OF THE INVENTION

Assays for analysis of biological processes are exploited for a variety of desired applications. For example, monitoring the activity of key biological pathways can lead to a better understanding of the functioning of those systems as well as those factors that might disrupt the proper functioning of those systems. In fact, various different disease states caused by operation or disruption of specific biological pathways are the focus of much medical research. By understanding these pathways, one can model approaches for affecting them to prevent the onset of the disease or mitigate its effects once manifested.

A stereotypical example of the exploitation of biological process monitoring is in the area of pharmaceutical research and development. In particular, therapeutically relevant biological pathways, or individual steps or subsets of individual steps in those pathways, are often reproduced or modeled in in vitro systems to facilitate analysis. By observing the progress of these steps or whole pathways in the presence and absence of potential therapeutic compositions, e.g., pharmaceutical compounds or other materials, one can identify the ability of those compositions to affect the in vitro system, and potentially beneficially affect an organism in which the pathway is functioning in a detrimental way. By way of specific example, reversible methylation of the 5' position of cytosine by methyltransferases is one of the most widely studied epigenetic modifications. In mammals, 5-methylcytosine (5-MeC) frequently occurs at CpG dinucleotides, which often cluster in regions called CpG islands that are at or near transcription start sites. Methylation of cytosine in CpG islands can interfere with transcription factor binding and is associated with transcription repression and gene regulation. In addition, DNA methylation is known to be essential for mammalian development and has been associated with cancer and other disease processes. Recently, a new 5-hydroxymethylcytosine epigenetic marker has been identified in certain cell types in the brain, suggesting that it plays a role in epigenetic control of neuronal function (S. Kriaucionis, et al., *Science* 2009, 324(5929): 929-30, incorporated herein by reference in its entirety for all purposes).

In contrast to determining a human genome, mapping of the human methylome is a more complex task because the methylation status differs between tissue types, changes with age, and is altered by environmental factors (P. A. Jones, et al., *Cancer Res* 2005, 65, 11241, incorporated herein by reference in its entirety for all purposes). Comprehensive, high-resolution determination of genome-wide methylation patterns from a given sample has been challenging due to the sample preparation demands and short read lengths characteristic of current DNA sequencing technologies (K. R. Pomraning, et al., *Methods* 2009, 47, 142, incorporated herein by reference in its entirety for all purposes).

Bisulfite sequencing is a currently used method for single-nucleotide resolution methylation profiling (S. Beck, et al., *Trends Genet* 2008, 24, 231; and S. J. Cokus, et al., *Nature* 2008, 452, 215, the disclosures of which are incorporated herein by reference in their entireties for all purposes). In another widely used technique, methylated DNA immunoprecipitation (MeDIP), an antibody against 5-MeC is used to enrich for methylated DNA sequences (M. Weber, et al., *Nat Genet* 2005, 37, 853, incorporated herein by reference in its entirety for all purposes). MeDIP has many advantageous attributes for genome-wide assessment of methylation status, but it does not offer as high base resolution as bisulfite treatment-based methods. In addition, it is also hampered by the same limitations of current microarray and second-generation sequencing technologies.

Research efforts aimed at increasing our understanding of the human methylome would benefit greatly from the development of a new methylation profiling technology that does not suffer from the limitations described above. Accordingly, there exists a need for improved techniques for detection of modifications in nucleic acid sequences, and particularly nucleic acid methylation.

Typically, modeled biological systems rely on bulk reactions that ascertain general trends of biological reactions and provide indications of how such bulk systems react to different effectors. While such systems are useful as models of bulk reactions in vivo, a substantial amount of information is lost in the averaging of these bulk reaction results. In particular, the activity of and effects on individual molecular complexes cannot generally be teased out of such bulk data collection strategies.

Nanopore sequencing has been demonstrated to be capable of identifying bases in a single nucleic acid strand passed through the nanopore at single base resolution. The bases can be differentiated by their differential blocking of the nanopore as they pass through the pore. While in some cases, modified bases may be identified by their current blocking characteristics, it can be difficult to differentiate these bases from the four canonical bases and from other modified bases. There exists a need for improved nanopore sequencing that provides more reliable information about the modified bases that occur in natural nucleic acids.

BRIEF SUMMARY OF THE INVENTION

In some aspects, the invention provides a method for sequencing a nucleic acid template and identifying modified bases therein comprising: providing a substrate having an upper solution above the substrate and a lower solution below the substrate, the substrate comprising a nanopore connecting the upper solution and lower solution, the nanopore sized to pass a single stranded nucleic acid; providing a voltage across the nanopore to produce a measurable current flow through the nanopore; controlling the rate of translation of a single stranded portion of the template nucleic acid through the pore with a processive enzyme associated with a template nucleic acid; measuring the current through the nanopore over time as it is translated through the nanopore; determining the sequence of a portion of the template nucleic acid as it translates through the pore using the measured current over time; and determining the presence of modified nucleic acids in the template nucleic acid by correlating changes in the rate of transport of the nucleic acid to changes through the nanopore to the kinetics of the processive enzyme from the interaction of the modified base with the processive enzyme.

The template nucleic acid can be sequenced multiple times. The processive enzyme can comprise a polymerase, exonuclease, or helicase activity. The processive enzyme can comprise a DNA polymerase. The DNA polymerase can have a 3' to 5' exonuclease activity. The processive enzyme can comprise a helicase.

In some aspects, the invention provides a method for sequencing a nucleic acid comprising: providing a substrate having an upper solution above the substrate and a lower solution below the substrate, the substrate comprising a nanopore connecting the upper solution and lower solution, the nanopore sized to pass a single stranded nucleic acid; providing a voltage across the nanopore to produce a measurable current flow through the nanopore; controlling the rate of translation of a single stranded portion of the template nucleic acid through the pore with a processive enzyme associated with the template nucleic acid; measuring the current through the nanopore over time as it is translated through the nanopore; and determining the sequence of a portion of the template nucleic acid as it translates through the pore using the measured current over time; wherein the template nucleic acid comprises hemi-genomic DNA comprising a genomic strand and a nascent strand. The nascent strand can be translated through the pore. The genomic strand can be translated through the pore. The genomic strand and nascent strand can be attached through a hairpin loop and both strands are translated through the pore.

The processive enzyme can comprise polymerase, exonuclease, or helicase activity. The processive enzyme can comprise a DNA polymerase. The DNA polymerase can have a 3' to 5' exonuclease activity. The processive enzyme can comprise a helicase.

The template nucleic acid can be sequenced multiple times.

In some aspects, the invention provides a nucleic acid template for nanopore sequencing comprising a strand comprising natural nucleic acid sequence and a synthetic nucleic acid sequence that is complementary to the natural nucleic acid sequence.

The nucleic acid template can comprise the natural sequence hybridized to the synthetic sequence, and the sequences connected through a hairpin loop. The natural sequence and the synthetic sequence can be part of a nucleic acid strand that is hybridized to a synthetic strand. The nucleic acid template can comprise a second synthetic sequence that is substantially identical with the natural sequence. The natural sequence can be 5' of the synthetic sequence. The natural sequence can be 3' of the synthetic sequence. The nucleic acid can comprise DNA and the natural sequence can comprise a genomic sequence.

In some aspects, the invention provides a method for sequencing a nucleic acid comprising: providing a substrate having an upper solution above the substrate and a lower solution below the substrate, the substrate comprising a nanopore connecting the upper solution and lower solution, the nanopore sized to pass a single stranded nucleic acid; providing a voltage across the nanopore to produce a measurable current flow through the nanopore; controlling the rate of translation of a single stranded portion of the template nucleic acid through the pore with a processive enzyme associated with a template nucleic acid; measuring the current through the nanopore over time as it is translated through the nanopore; and determining the sequence of a portion of the template nucleic acid as it translates through the pore using the measured current over time; wherein the template nucleic acid comprises a strand comprising natural nucleic acid sequence and a synthetic nucleic acid sequence that is complementary to the natural nucleic acid sequence, whereby both the natural nucleic acid sequence and the synthetic nucleic acid sequences are translated through the pore.

The method can further comprise using sequence information from the synthetic sequence to identify a modified base present in the natural nucleic acid sequence.

The template nucleic acid can further comprise a second synthetic sequence that is substantially identical with the natural sequence. The processive enzyme can comprise polymerase, exonuclease, or helicase activity. The processive enzyme can comprise a DNA polymerase. The processive enzyme can comprise a helicase.

The template nucleic acid can be sequenced multiple times.

In some aspects, the invention provides a method for nanopore sequencing with reduced error comprising: providing a substrate having an upper solution above the substrate and a lower solution below the substrate, the substrate comprising a plurality of nanopores connecting the upper solution and lower solution, the nanopores sized to pass single stranded nucleic acids; providing a voltage across the nanopores to produce a measurable current flow through the nanopores; measuring the current through the nanopores over time as the nucleic acid templates are translated through the nanopore; measuring the sequence of a portion of a plurality template nucleic acids as they translate through the pore using the measured current over time; wherein some of the plurality of template nucleic acids comprise the same sequence, and wherein the sequence of some of the plurality of nucleic acids is measured under one set of reaction conditions, and the sequence of some of the plurality of nucleic acids is measured under a second set of reaction conditions, where the first and second reaction conditions each provide different error profiles, and determining a sequence by combining the measured sequences under the first and second reaction conditions to obtain a reduced error rate than for a sequence determined under one reaction condition.

The method can further comprise controlling the rate of translation of a single stranded portion of the template nucleic acid through the pore with a processive enzyme associated with a template nucleic acid.

The two reaction conditions can comprise two different types of nanopores. The two reaction conditions can comprise two different types of processive enzymes. The combined sequences can represent sequences on a single molecule. The combined sequences can represent sequences on different molecules.

The change in reaction condition can comprise a change in the temperature, pH, or in the level of divalent cation or a combination of these.

BRIEF DESCRIPTION OF THE DRAWINGS

FIGS. 4A and 4B illustrate a method of the invention in which modified base detection and sequencing is carried out in a nanopore with a helicase translating enzyme. In FIG. 4A, nucleotides 430, 432, and 434 are within the nanopore and nucleotide 414 is associated with the enzyme, in FIG. 4B, nucleotides 430, 432, and 434 have passed throughout the nanopore and nucleotide 414 is within the nanopore.

FIGS. 5A-5D illustrate a method of the invention in which repeated modified base detection and sequencing is carried out on the same molecule in a nanopore with a helicase translating enzyme. FIG. 5A shows a DNA strand being sequenced with nanopore extending through a substrate. In FIG. 5B the applied voltage across the nanopore is reversed in order to pull the DNA strand up into the pore. FIG. 5C shows how a DNA strand can re-anneal with its complementary strand. FIG. 5D illustrates how the process can be repeated.

FIGS. 6A-6D illustrate how nanopore loading and sequencing/modified base detection are carried out with a polymerase translating enzyme and a circular template. In FIG. 6A, a complex is formed between the circular nucleic acid and the polymerase enzyme. In FIG. 6B, polymerase mediated nucleic acid synthesis is carried out around the circle until it begins to displace the nascent strand. In FIG. 6C, the complex having the extended nascent strand is loaded into a nanopore. In FIG. 6D, sequencing and detection of base modification is carried out by adding the reagents for polymerase mediated nucleic acid added, and applying a voltage to hold the polymerase on the nanopore and to provide a force on the strand.

FIGS. 7A-7D illustrate how nanopore loading and sequencing/modified base detection are carried out with a helicase translating enzyme. In FIG. 7A, a helicase is mixed with a nucleic acid. In FIG. 7B, the helicase forms a complex with the nucleic acid. In FIG. 7C, a voltage is applied across the nanopore to draw the strand into the pore. In FIG. 7D, the helicase activity pulls apart the strands, paying out one strand through the pore as the voltage applied pulls the strand through the pore at a rate controlled by the helicase.

FIG. 8A shows an example of the structure of a template nucleic acid having a splint strand hybridized so as to prevent formation of the hairpin structure until its removal. FIG. 8B shows how the hairpin forms on one side of the nanopore after the splint strand has been displaced, forming a blockage.

FIGS. 12A-12C show alternative adaptors for making hemi-natural nucleic acid templates. FIG. 12A shows an adaptor with a hairpin that can be used, for example to put a hairpin at one end of the double stranded natural nucleic acid fragment. FIG. 12B shows an adaptor that can be used to produce a different overhang region on each strand. FIG. 12C illustrates an adaptor having a primer with a 5' non-hybridized portion that can be used to produce a 5' single stranded overhang for loading into the nanopore.

FIG. 13 illustrates the end of a template for loading having an overhang region for loading into the nanopore, and a non-complementary region in the other strand.

FIGS. 14A-14G show representative structures for the hemi-natural nucleic acid (e.g. hemi-genomic DNA) templates of the invention. FIGS. 14A, 14B, 14C, and 14D show different types of templates with a natural sequence, a complementary sequence, and a hairpin nucleic acid connecting the sequences. FIG. 14E shows a template nucleic acid with a natural sequence and a synthetic sequence connected by a connecting nucleic acid in one strand, with a complementary synthetic strand hybridized to it. FIG. 14F shows a template nucleic acid having a natural sequence and a synthetic sequence on the same strand connected by a connecting nucleic acid. FIG. 14G shows a template nucleic acid with a natural sequence connected through a connector nucleic acid to synthetic sequence.

FIG. 15A shows a method for obtaining a template for nanopore sequencing having a natural sequence and a synthetic sequence that are substantially identical with a complementary synthetic sequence between. FIG. 15B shows a method for obtaining a template for nanopore sequencing having a natural sequence and a synthetic sequence that are substantially identical with a complementary natural sequence between.

DETAILED DESCRIPTION OF THE INVENTION

Figure 1:
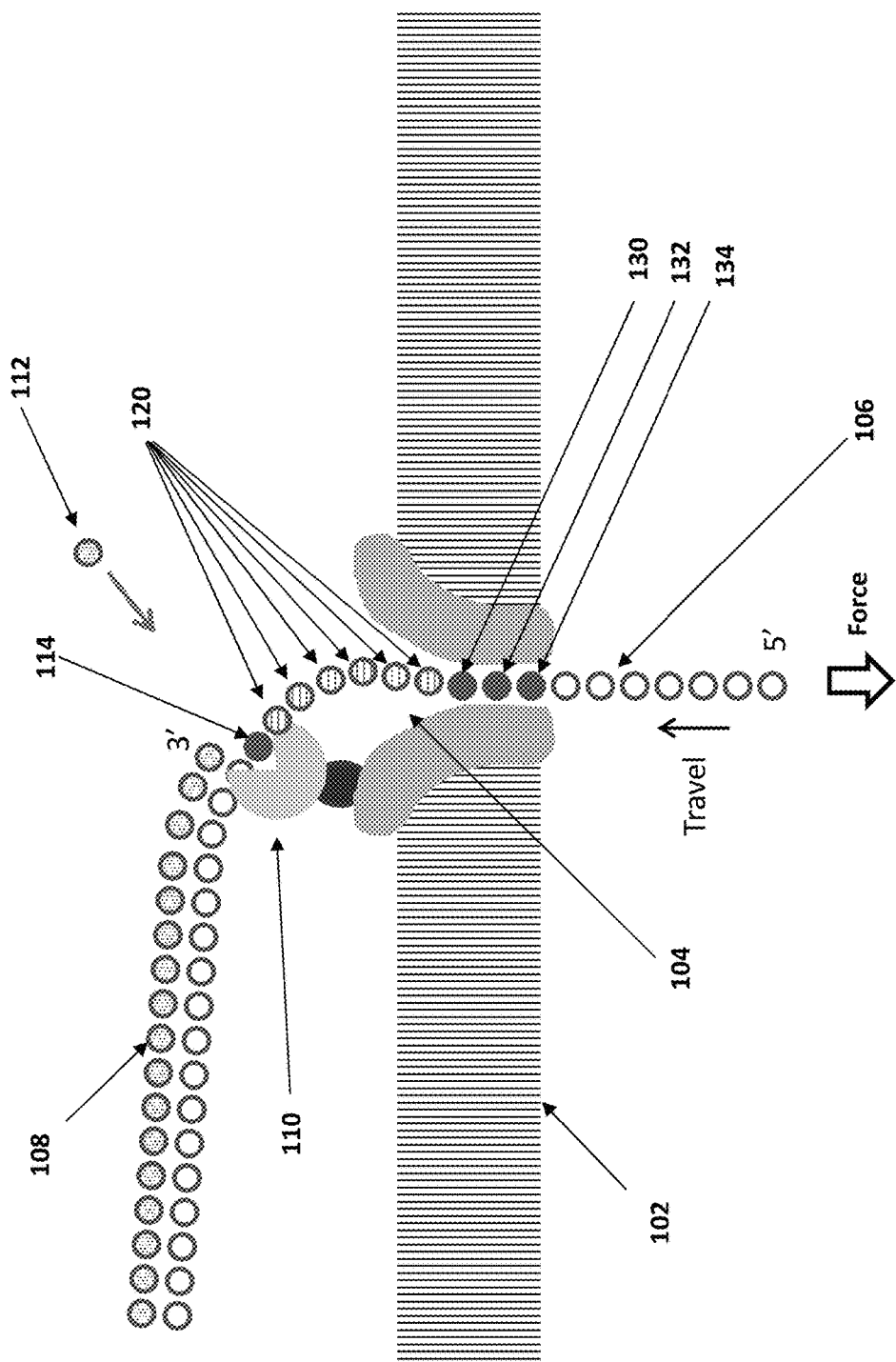
FIG. 1 illustrates a method of the invention in which modified base detection and sequencing is carried out in a nanopore with a polymerase translating enzyme.

The invention provides devices, methods, and compositions for sequencing nucleic acids and for identifying modified bases using nanopores. Single-stranded nucleic acids are transported through a nanopore using at translating enzyme to control the rate of transport the nucleic acid. An applied voltage passes ions through the nanopore while the nucleic acid is being translated. Each of the bases in the nucleic acid blocks the pore in a measurably different way, allowing for identification of the bases in the strand, and thereby sequencing the nucleic acid. The bases are identified, for example, by current or capacitance changes. The invention allows for the improved identification of non-natural, or modified bases by correlating the kinetics of passage of the bases through the pore with the kinetics of the translating enzyme. We have determined that under certain conditions, the kinetics of the translating enzyme can be directly determined by measuring the transport of the bases through the nanopore. In particular, the applied voltage is adjusted to apply a force to the translated nucleic acid strand such that the rate of translation of the nucleic acid through the pore is substantially equivalent to the rate of processing the nucleic acid by the translating enzyme.

We have found that sequencing of nucleic acids, and the identification of modified nucleic acids can be significantly enhanced by using a hemi-natural nucleic acid, and in particular a hemi-genomic DNA strand. In a hemi-natural nucleic acid, one strand is the natural strand, e.g. the strand from the organism, and the other strand is a synthesized (or nascent) strand. The nascent strand is typically produced with only the four canonical bases (A, G, C and T, or A, G, C and U). An advantage of using hemi-natural nucleic acids in nanopore sequencing of nucleic acids with modified bases is that only one of the strands that is interacting with the translating enzyme will contain the modified bases. This can significantly reduce the complexity of the calling of the modified base in some cases as compared to analyzing a fully natural nucleic acid.

There are two modes for using hemi-natural nucleic acids in nanopore sequencing, one in which the nascent strand is transported through the pore, and the other, in which the genomic strand is translated through the pore. When passing only the nascent strand of the hemi-natural nucleic acid through the pore, no modified bases are translated through the pore, and yet their presence can be determined by the changes in rate that they cause at the transporting enzyme. Use of the nascent strand has the advantage that, since the modified bases do not translate through the pores, one only has to call out the identity of four bases using current or capacitance, and there is no need uncertainty caused by passage of a different base through the pore. This method can also be useful with modified bases that have structures that make it difficult for the base to pass through the pore. This can be the case, for example, for a glucosylated base, where the sugar moiety is large enough that it may not make it through the nanopore.

In some cases, the genomic strand of the hemi-natural nucleic acid can be translated through the nanopore. For this mode, the modified base will pass through the nanopore either prior to, or after the modified base interacts with the translating protein. While this method requires calling of the modified base in addition to the four canonical bases by their relative blockage of the nanopore, it provides an additional indication of the presence of the modified base, allowing in some cases for enhanced accuracy. This mode allows for the combination of the kinetics at the translating enzyme and the relative blockage of current at the nanopore to be used to identify a modified base. Under the appropriate conditions, the modified base will pass through the nanopore a specific number of bases away from the identifiable kinetic event at the translating enzyme.

We have found that hemi-natural nucleic acids, and in particular, hemi-genomic DNA can be used in nanopore sequencing even where one is not attempting to call out the modified bases in a nucleic acid sample. For example, if genomic DNA is directly used in nanopore sequencing, the modified bases in the DNA can give rise to errors in calling the identity of the four canonical bases. While this issue can be ameliorated by amplifying the genomic DNA and sequencing completely synthetic DNA, each round of amplification can give rise to defects, which will produce errors in the measured sequence. By sequencing the nascent strand of the hemi-genomic DNA, one gets the benefit that only the four canonical bases are passed through the nanopore, and since there is only one replication step to form the nascent strand, replication errors are minimized.

Some aspects of the invention provide for repeated sequencing of the same molecule multiple times. In any sequencing method, including nanopore sequencing, there will be some level of errors in base calling. In addition, even for a reaction with a specific rate constant, kinetic rates measured on the single molecule level will typically result in a range of rate values for that given process, making base calling by rate difficult from only a single value. The methods of the invention are generally performed repeatedly on the same molecule providing significantly improved accuracy. Repeated sequencing approaches are described in more detail below.

In order to perform repeated sequencing on the same molecule, it is generally desirable that the molecule not be released from the pore between sequence determinations. The templates of the instant invention generally have blocking groups attached to them (typically at the end). The blocking groups prevent the release of the template from the pore under sequencing conditions. In some cases, the blocking groups are located on both ends of a strand that is sequenced, preventing it from being released on either side of the pore. In some cases, reversible blocking groups are employed, allowing for the release of the nucleic acid strand after sequencing is completed. We have found that hairpin regions in the nucleic acid strand can be used to prevent the nucleic acid strand from being released, for example using a nanopore that is sized to pass a single strand but not a double strand. By increasing the applied voltage, one can provide enough force to peel away the hairpin to allow release. In preferred aspects, a hairpin stopper is ligated to the end of the strand to be sequenced. The hairpin stopper has two complementary sequences and an intermediate hairpin region between them. A splint oligonucleotide is hybridized to the strand before loading. Upon loading, the splint oligonucleotide is peeled away at the pore, and the complementary regions of the hairpin stopper form a hairpin after passing through the pore. This hairpin acts as a blocker during sequencing the strand. The strand can be subsequently removed from the pore by applying enough drive voltage to peel apart the hairpin, or to change the stringency of the medium to open up the complementary regions of the hairpin.

The invention is generally described by reference to a single nanopore, but the invention anticipates using arrays of nanopores from e.g. 10 nanopores to about 10 million nanopores. In some cases arrays of 10 nanopores to 1000 nanopores are used. In some cases, arrays of nanopores of about 100 to about 10,000 nanopores are used. In some cases, arrays of nanopore from about 1,000 to about 1 million nanopores are used. Methods of carrying out nanopore sequencing in arrays of nanopores is described, for example in U.S. Ser. No. 13/083,320 filed Apr. 8, 2011.

The mode that is applied can be chosen based on the type of translating enzyme that is used, and which strand is being translated through the pore. For example, the mode that is selected can depend on whether the translating enzyme is a polymerase, an exonuclease, or a helicase.

FIG. 1 shows an example of an embodiment of the invention using a polymerase enzyme as the translating enzyme in which the polymerase pulls the single stranded nucleic acid up through the pore as it adds nucleotides to a growing strand. A substrate 102 has a nanopore 104 extending through it. As shown in the figure, the substrate 102 comprises a lipid bilayer, and the nanopore 104 is formed using a biological transmembrane protein such as MspA. The embodiment shown could be carried out with other suitable substrates and with a nanopore such as a solid state or hybrid nanopore. The polymerase enzyme 110 is associated with a region of a nucleic acid strand (e.g. DNA) 106 which extends through the nanopore with its 5' end. The nucleic acid strand experiences a force pulling it into the pore due to a voltage that is applied across the nanopore. Hybridized to a portion of nucleic acid strand 106 is complementary strand 108 that ends at a 3' terminus hybridized to strand 106. A polymerase enzyme 110 is associated with nucleic acid strand at the position of the 3' terminus of complementary strand 108. In the figure, the polymerase enzyme is shown attached to the substrate (e.g. to the biological nanopore). In some cases, the polymerase is not attached, but is held in place by the force of the electric field pulling on the nucleic acid strand 106.

The medium surrounding the polymerase enzyme has the components required for nucleic acid synthesis including nucleotides and cofactors. As the polymerase adds nucleotides such as 112 to the growing complementary strand 108, the nucleic acid strand 106 is pulled up into the nanopore in the direction against the force on the nucleic acid strand from the voltage across the pore. By controlling the force on nucleic acid strand 106 (e.g. by controlling the applied voltage), the number of bases 120 between the active site of the enzyme and nanopore will remain relatively constant throughout the process. Where the number of bases between the enzyme and the nanopore is constant, the rate of passage of bases through the nanopore will be equivalent to the rate of nucleic acid synthesis by the polymerase enzyme. Where the number of bases 120 is controlled, we have determined that changes in the rate of nucleic acid synthesis due to the presence of modified bases can be used to identify modified bases in the nucleic acid strand 106.

For example, consider a modified base 114 in nucleic acid strand 106 that slows or otherwise modifies the nucleic acid synthesis rate. At the instant the rate of polymerization is slowed by base 114, the rate of transport of bases through the nanopore is also slowed by the same amount. In the figure, the nanopore has a region in which the presence of three bases 130, 132, and 134 determines the current through the pore. By knowing the current level for all of the triads of bases, the bases can be called at single base resolution as the bases are drawn through the nanopore. The slowing of the polymerase by base 114 is measured as a slowing in the translation of bases 130, 132, and 134 through the pore. If the number of bases 120 between the nanopore and the modified base at the position the base slows the polymerase is known, then the presence of the modified base at that position can be determined. In some cases, modified bases can produce kinetic changes at positions other than when the modified base is in the active site of the enzyme. In fact, the changes in kinetics can occur before, during, or after the modified base is in the active site of the polymerase. In some cases, the modified base can cause a series of kinetic changes, resulting in a distinctive pattern of kinetic changes. The pattern of kinetic changes can involve 2, 3, 4, 6, 7, 8, or more kinetic changes, some or all of which can occur before, during, or after the modified base is in the active site of the polymerase. The kinetic change can be a change in the time for a one base transition in the current or capacitance signal. The kinetic change can also involve other measured parameters such as the noise level in the signal, or the shape of the transition signal, for example, noise color as described in more detail below.

Sequencing is performed as nucleotides added from solution, e.g. 112, lengthen complementary strand 108 and thereby pull the single nucleic acid strand into the pore. Consider the case in which base 134 has a modified base. As the nucleic acid strand is pulled up into the pore, base 134 will be present during three single base transitions. Since base 134 is modified, it will generally have a different signal than any of the canonical bases (See e.g. Mirsaidov, U. et al. Nanoelectromechanics of methylated DNA in a synthetic nanopore. Biophys. J. 96, L32-L34 (2009); Wanunu, M. et al. Discrimination of methylcytosine from hydroxymethylcytosine in DNA molecules. J. Am. Chem. Soc. 133, 486-492 (2010) and Botstein, D. & Risch, N. Discovering genotypes underlying human), each of which is incorporated by reference herein for all purposes. Thus, for three separate single base transitions, the presence of the modified base is detected. Then, some number of bases later, depending on the number of bases between the nanopore measurement position and the position at which the base affects the kinetics of the polymerase enzyme, a kinetic change from the presence of the base as it interacts with the translating enzyme will be measured. For this system, the kinetics of the interaction of the modified base with the polymerase enzyme, and the distinct current signature for the base as it passes through the pore can be used together to call out the identity and position of the modified base.

The number of bases between when the base is in the nanopore and when it is in the position to provide a kinetic signature can be determined by sequencing and simultaneously determining kinetics of the base modification using a known sample. By correlating the measured kinetics with the known sequence of bases as they pass through the nanopore, the number of bases between the bases in the nanopore and position of the base when providing the kinetic signature can be determined. Since, in accordance with the instant invention, conditions are used which keep the number of bases between the bases in the nanopore and the base in the active site constant, once the relevant number of bases is determined for known samples, it can be used to identify the positions of modified bases in unknown samples.

The nucleic acid can comprise DNA, RNA, or mixtures of DNA and RNA. For example, in FIG. 1, both of the strands can be DNA, and the enzyme is a DNA polymerase. Alternatively, the strand passing through the nanopore can be RNA, and the nascent strand can be DNA, and the enzyme is a reverse transcriptase. Other combinations including where both strands are RNA or where either strand has RNA and DNA portions can be used.

Figure 2:
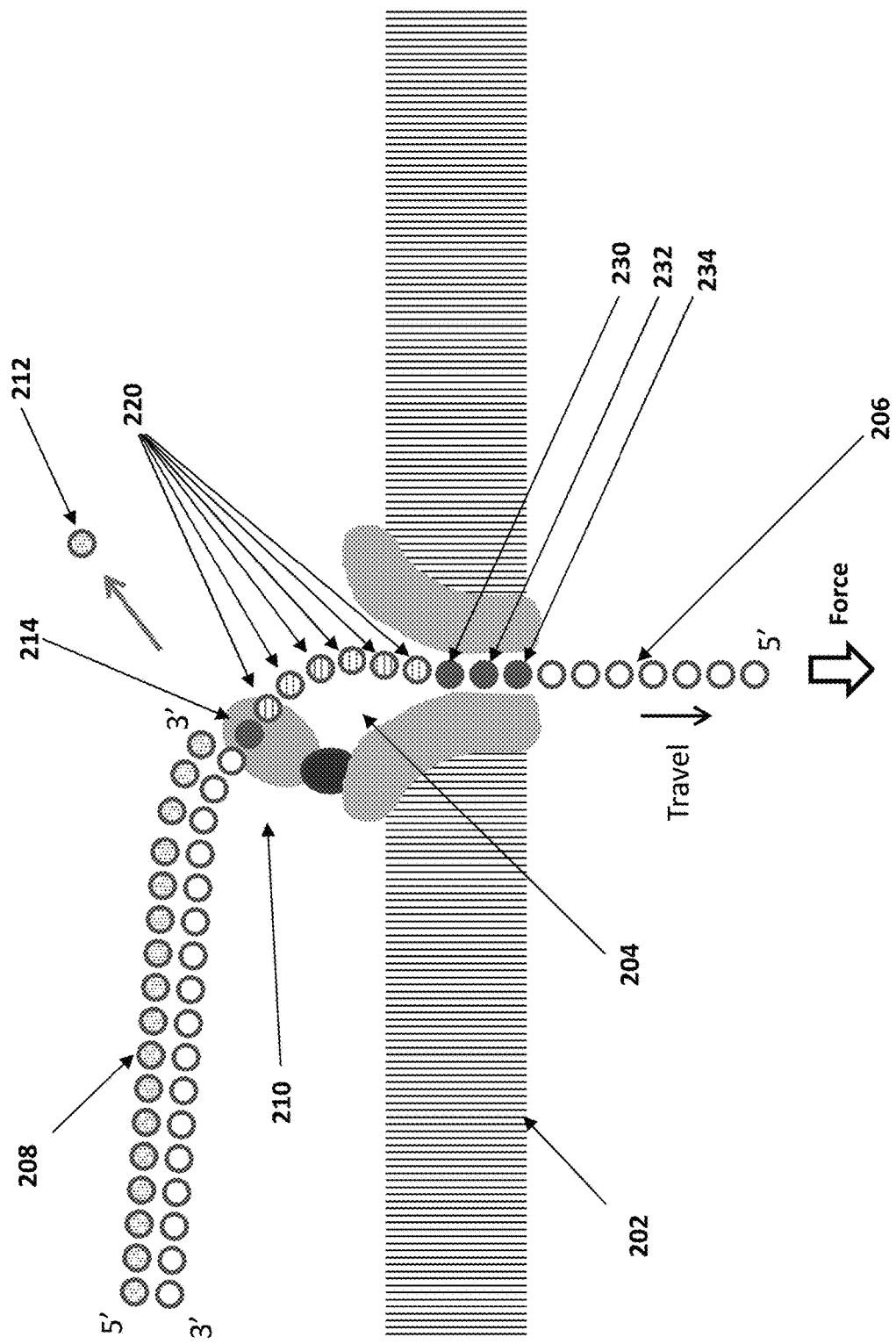
FIG. 2 illustrates a method of the invention in which modified base detection and sequencing is carried out in a nanopore with an exonuclease translating enzyme.

FIG. 2 shows an example of an embodiment of the invention using a 3' to 5' exonuclease enzyme as the translating enzyme in which the enzyme pays out the single stranded nucleic acid through the pore as it removes nucleotides from a complementary strand. The term exonuclease enzyme refers to an enzyme having exonuclease activity. Thus, for example, an exonuclease enzyme could refer to a polymerase enzyme having exonuclease activity. A substrate 202 has a nanopore 204 extending through it. As shown in the figure, the substrate 202 comprises a lipid bilayer, and the nanopore 204 is formed using a biological transmembrane protein such as MspA. The embodiment shown can be carried out with other suitable substrates and with a nanopore such as a solid state or hybrid nanopore. The exonuclease enzyme 210 is associated with a region of a nucleic acid strand (e.g. DNA) 206 which extends through the nanopore with its 5' end. The nucleic acid strand experiences a force pulling it into the pore due to a voltage that is applied across the nanopore. Hybridized to a portion of nucleic acid strand 206 is complementary strand 208 that ends at a 3' terminus, hybridized to strand 206. An exonuclease enzyme 210 is associated with nucleic acid strand at the position of the 3' terminus of complementary strand 208. In the figure, the exonuclease enzyme is shown attached to the substrate (e.g. to the biological nanopore). In some cases, the exonuclease is not attached, but is held in place by the electric field applying a force pulling on the nucleic acid strand 106.

The medium surrounding the exonuclease enzyme has the components required for nucleic acid synthesis including appropriate cofactors. As the exonuclease removes nucleotides such as 212 from the growing complementary strand 208, the nucleic acid strand 206 is paid out into the nanopore in the direction of the force on the nucleic acid strand from the voltage across the pore. By controlling the force on nucleic acid strand 206 (e.g. by controlling the applied voltage), the number of bases 220 between the active site of the enzyme and nanopore will remain relatively constant throughout the process. Where the number of bases between the exonuclease enzyme and the nanopore is constant, the rate of passage of bases through the nanopore will be equivalent to the rate of nucleic acid excision by the exonuclease enzyme. Where the number of 220 is controlled, we have determined that changes in the rate of nucleic acid synthesis due to the presence of modified bases can be used to identify modified bases in the nucleic acid strand 206.

For example, consider a modified base 214 in nucleic acid strand 206 that slows or otherwise modifies the base excision rate. At the time the rate of polymerization is slowed by base 214, the rate of transport of bases through the nanopore is also slowed by the same amount. In the figure, the nanopore has a region in which the presence of three bases 230, 232, and 234 determines the current through the pore. By knowing the current level for all of the triads of bases, the bases can be called at single base resolution as the bases are drawn through the nanopore. The slowing of the exonuclease by base 214 is measured as a slowing in the translation of bases 230, 232, and 234 through the pore. If the number of bases 320 between the nanopore and the modified base at the position the base slows the polymerase is known, then the presence of the modified base at that position can be determined. In some cases, modified bases can produce kinetic changes at positions other than when than when the modified base is in the active site of the enzyme. In fact, the changes in kinetics can occur before, during, or after the modified base is in the active site of the exonuclease. In some cases, the modified base can cause a series of kinetic changes, resulting in a distinctive pattern of kinetic changes. The pattern of kinetic changes can involve 2, 3, 4, 6, 7, 8, or more kinetic changes, some or all of which can occur before, during, or after the modified base is in the active site of the exonuclease. The kinetic change can be a change in the time for a one base transition in the current or capacitance signal. The kinetic change can also involve other measured parameters such as the noise level in the signal, or the shape of the transition signal, for example, noise color as described in more detail below.

Sequencing is performed as nucleotides, e.g. 212, are removed by the exonuclease from strand 208, shortening complementary strand 208 and thereby paying out the single nucleic acid strand 206 into the pore. Consider the case in which base 214 has a modified base. As the nucleic acid strand is paid out through the pore, base 214 will be interacting with the exonuclease, modifying its rate. At the time that base 214 is modifying the rate of the exonuclease enzyme, buses 230, 232, and 234 are in the nanopore, and their sequence is being determined. Then, some number of bases later, base 214 will pass through the nanopore. As it passes through the nanopore, the presence of the modified base can be determined, for example, by its current blockage characteristics. It can be useful to use a hemi-natural nucleic acid for this method in which strand 206 comprises a natural nucleic acid, and strand 208 comprises a synthetic nucleic acid. Using hemi-natural nucleic acid ensures that the measured kinetic changes are due only to bases in the genomic strand 206.

For this system, the kinetics of the interaction of the modified base with the exonuclease enzyme, and the distinct current signature for the base as it passes through the pore can be used together to call out the identity and position of the modified base.

Another approach is one in which strand 208 comprises a natural nucleic acid (genomic DNA). In this case, base 212 in strand 208 (prior to release) comprises a modified base. The base 212 can cause kinetic changes in the exonuclease enzyme as it interacts with the enzyme prior to or during its excision. These characteristic kinetic changes can provide the information that base 212 is a modified base, and where the number of bases between the kinetic changes at the exonuclease enzyme and the bases in the nanopore is known (as provided herein), the position of the modified base 212 on complementary strand 208 can be established. For this approach, it is useful to use hemi-genomic DNA in which strand 208 comprises genomic DNA, and strand 206 comprises synthesized DNA.

Figure 3:
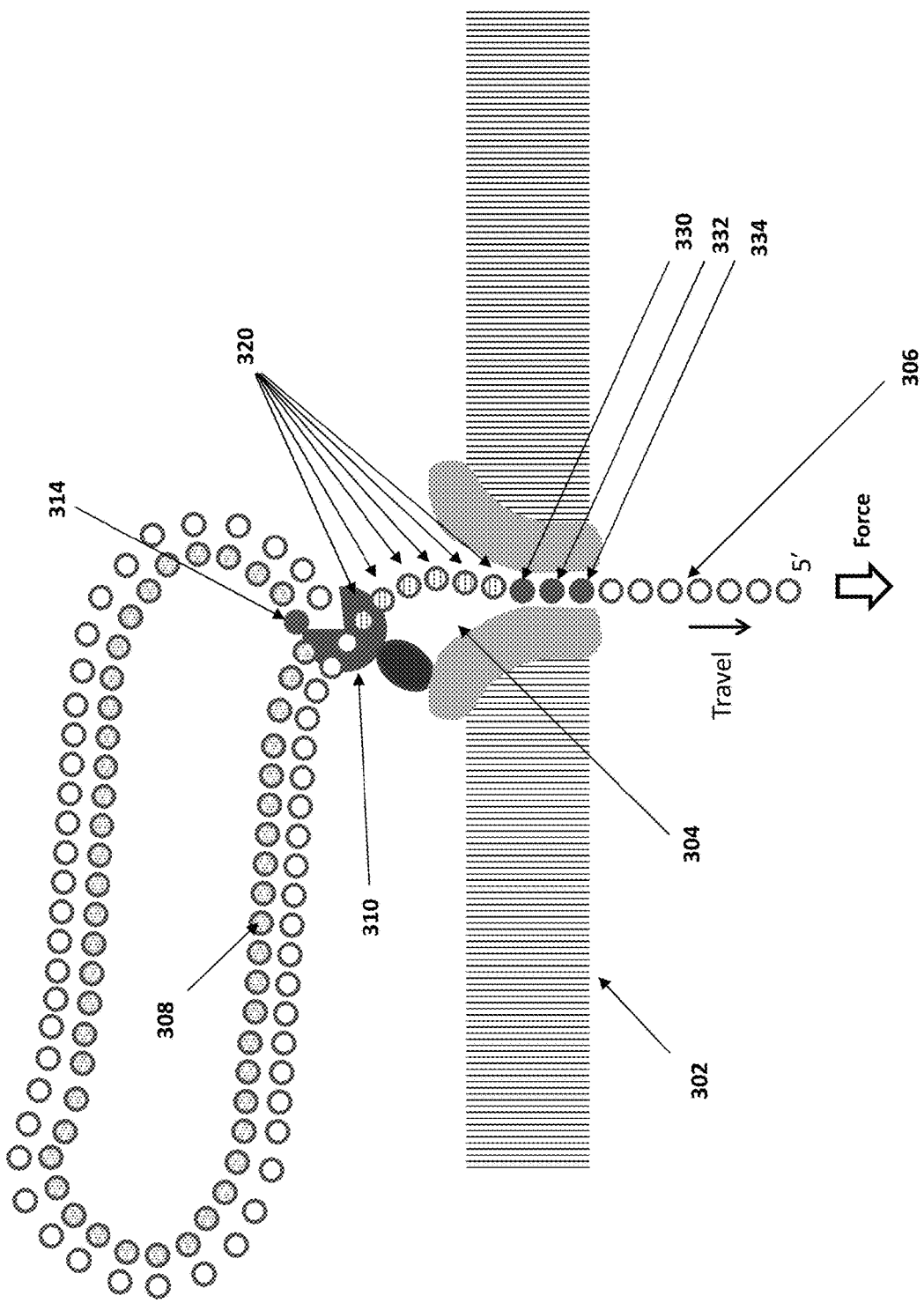
FIG. 3 illustrates a method of the invention in which modified base detection and sequencing is carried out in a nanopore with a polymerase translating enzyme.

FIG. 3 shows another example of an embodiment of the invention using a polymerase enzyme having strand displacement activity. In this method, the polymerase acts as the translating enzyme wherein the polymerase pays out a single stranded nascent nucleic acid through the pore as it adds nucleotides to a growing strand. A substrate 302 has a nanopore 304 extending through it. As shown in the figure, the substrate 302 comprises a lipid bilayer, and the nanopore 304 is formed using a biological transmembrane protein such as MspA. The embodiment shown could be carried out with other suitable substrates and with a nanopore such as a solid state or hybrid nanopore. The polymerase enzyme 310 is associated with a region of a circular nucleic acid strand (e.g. DNA) 208, and it synthesizes a nascent strand 306 complementary to strand 308. Strand 306 extends through the nanopore with its 5' end. The nucleic acid strand 306 experiences a force pulling it into the pore due to a voltage that is applied across the nanopore. In the figure, the polymerase enzyme is shown attached to the substrate (e.g. to the biological nanopore). In some cases, the polymerase is not attached, but is held in place by the force of the electric field pulling on the nucleic acid strand 306.

The medium surrounding the polymerase enzyme has the components required for nucleic acid synthesis including nucleotides and cofactors. As the polymerase adds nucleotides to the growing complementary strand 306, the strand 306 is paid out through the nanopore in the direction of the force on the nucleic acid strand from the voltage across the pore. By controlling the force on nucleic acid strand 306 (e.g. by controlling the applied voltage), the number of bases 120 between the active site of the enzyme and nanopore will remain relatively constant throughout the process. Where the number of bases between the enzyme and the nanopore is constant, the rate of passage of bases through the nanopore will be equivalent to the rate of nucleic acid synthesis by the polymerase enzyme. Where the number of bases 320 is controlled, we have determined that changes in the rate of nucleic acid synthesis due to the presence of modified bases can be used to identify modified bases in the circular nucleic acid strand 306. Here, hemi-natural nucleic acid is used as strand 308 represents a natural nucleic acid, and strand 306 is a synthetic strand.

For example, consider a modified base 314 in nucleic acid strand 308 that slows or otherwise modifies the nucleic acid synthesis rate. At the time the rate of polymerization is slowed by base 314, the rate of transport of bases through the nanopore is also slowed by the same amount. In the figure, the nanopore has a region in which the presence of three bases 330, 332, and 334 determines the current through the pore. By knowing the current level for all of the triads of bases, the bases can be called at single base resolution as the bases are drawn through the nanopore. The slowing of the polymerase by base 314 is measured as a slowing in the translation of bases 330, 332, and 334 through the pore. If the number of bases 320 between the nanopore and the modified base at the position the base slows the polymerase is known, then the presence of the modified base at that position can be determined. In some cases, modified bases can produce kinetic changes at positions other than when than when the modified base is in the active site of the enzyme. In fact, the changes in kinetics can occur before, during, or after the modified base is in the active site of the polymerase. In some cases, the modified base can cause a series of kinetic changes, resulting in a distinctive pattern of kinetic changes. The pattern of kinetic changes can involve 2, 3, 4, 6, 7, 8, or more kinetic changes, some or all of which can occur before, during, or after the modified base is in the active site of the polymerase. The kinetic change can be a change in the time for a one base transition in the current or capacitance signal. The kinetic change can also involve other measured parameters such as the noise level in the signal, or the shape of the transition signal, for example, noise color as described in more detail below. Sequencing is performed as nucleotides added from solution lengthen complementary strand 306 and thereby pay out the single nucleic acid strand through the pore.

FIG. 4 shows an example of an embodiment of the invention using a helicase enzyme as the translating enzyme in which the helicase pays out the single stranded nucleic acid through the pore as it separates two DNA strands. In FIG. 4A substrate 402 has a nanopore 404 extending through it. As shown in the figure, the substrate 402 comprises a lipid bilayer, and the nanopore 404 is formed using a biological transmembrane protein such as MspA. The embodiment shown could be carried out with other suitable substrates and with a nanopore such as a solid state or hybrid nanopore. The helicase enzyme 410 is associated with a region of a DNA strand 406 which extends through the nanopore. Depending on how the sample is loaded, the helicase can either pay out through the pore a strand having a 5' end or a strand having a 3' end. Controlling which end is extended into the nanopore can be controlled by controlling which of the strands has an over-hanging single stranded portion at its end. The nucleic acid strand experiences a force pulling it into the pore due to a voltage that is applied across the nanopore. The helicase can either be attached to the substrate, or it can be held in place by the force of the electric field pulling on the nucleic acid strand 306.

The medium surrounding the polymerase enzyme has the components required for helicase activity including, where required, ATP. As the helicase separates the double stranded DNA, DNA strand 406 is paid out through the nanopore in the direction of the force on the nucleic acid strand from the voltage across the pore. By controlling the force on nucleic acid strand 406 (e.g. by controlling the applied voltage), the number of bases 420 between the active site of the enzyme and nanopore will remain relatively constant throughout the process. Where the number of bases between the enzyme and the nanopore is constant, the rate of passage of bases through the nanopore will be equivalent to the rate of separation of DNA strands by the helicase enzyme. Where the number of bases 120 is controlled, we have determined that changes in the rate of nucleic acid synthesis due to the presence of modified bases can be used to identify modified bases in the nucleic acid strand 406.

In some cases, the helicase is initiated only after it is loaded. The helicase can be initiated by adding metal cofactors, adding ATP or an ATP analog, or using a helicase that is inhibited, and adding a reagent that removes an inhibitor. For example, the template strand can have a blocking group on strand 408 preventing the helicase from separating the strands. A group that removes the blocking group, e.g. a single-stranded restriction enzyme that breaks the strand can be added. Blockers for helicase include streptavidin, an abasic site, an O-Me group, a pyrimidine dimer, 8-OxoG or a crosslinked protein. The blocking group can be built into the hemi-natural nucleic acid during sample preparation.

Consider a modified base 414 in nucleic acid strand 406 that slows or otherwise modifies the helicase rate. At the instant the rate is slowed by base 414, the rate of transport of bases through the nanopore is also slowed by the same amount. In the figure, the nanopore has a region in which the presence of three bases 430, 432, and 434 determines the current through the pore. By knowing the current level for all of the triads of bases, the bases can be called at single base resolution as the bases are drawn through the nanopore. The slowing of the helicase by base 414 is measured as a slowing in the translation of bases 430, 432, and 434 through the pore. If the number of bases 420 between the nanopore and the modified base at the position the base slows the polymerase is known, then the presence of the modified base at that position can be determined. In some cases, modified bases can produce kinetic changes at positions other than when than when the modified base is in the active site of the enzyme. In fact the changes in kinetics can occur before, during, or after the modified base is in the active site of the helicase. In some cases, the modified base can cause a series of kinetic changes, resulting in a distinctive pattern of kinetic changes. The pattern of kinetic changes can involve 2, 3, 4, 6, 7, 8, or more kinetic changes, some or all of which can occur before, during, or after the modified base is in the active site of the helicase. The kinetic change can be a change in the time for a one base transition in the current or capacitance signal. The kinetic change can also involve other measured parameters such as the noise level in the signal, or the shape of the transition signal, for example, noise color as described in more detail below.

Sequencing is performed as the helicase separates the DNA strands, paying out the single nucleic acid strand 406 into the pore. FIG. 4 illustrates a case in which base 414 or base 416 is a modified base. As the nucleic acid strand is paid out through the pore, base 414 (or 416) will be interacting with the helicase, modifying its rate. At the time that base 414 (or 416) is modifying the rate of the helicase enzyme, bases 430, 432, and 434 are in the nanopore, and their sequence is being determined. FIG. 4B illustrates the status at a time some number of bases later when base 414 passes through the nanopore. As it passes through the nanopore, the presence of the modified base 414 can be determined, for example, by its current blockage characteristics. Alternatively, if base 416 is the modified base, base 416 never translates through the nanopore. It can be useful to use a hemi-genomic DNA for this method in which either strand 406 or strand 408 comprises genomic DNA, and the other strand comprises a synthetic nucleic acid.

Repeated Modified Base Detection on the Same Nucleic Acid Molecule

In order to obtain high quality information on the kinetics of single molecule processes, it is often useful to measure multiple passes. An aspect of the invention is using repeated sequencing and modified base detection on the same molecule. Repeated sequencing can be carried out with the instant invention in different ways depending on the translating enzyme that is used. FIG. 5 illustrates repeated sequencing and modified base detection according to the invention where the translating enzyme is a helicase. FIG. 5A shows a DNA strand 506 being sequenced with nanopore 504 extending through substrate 502 as described above. A voltage is applied that provides a force tending to pull DNA strand 506 into nanopore 504. The voltage level is selected such that the helicase is held against the substrate proximate to the nanopore entrance, and such that the number of bases between a modified base interacting with the helicase and the bases within the nanopore are substantially constant. As the helicase 510 separates the DNA strands 506 and 508, DNA strand 506 is paid through the nanopore at a rate that is set by the helicase activity. As described above, the presence and locations of modified bases either on strand 506 or strand 508 are measured using the kinetic signatures for that type of base. The modified base can be, for example 5-methyl-C.

After performing sequencing in this manner over a portion or all of strand 506, the applied voltage across the nanopore is reversed in order to pull strand 506 up into the pore as shown in step I and FIG. 5B. A blocking group 530 is typically used to prevent strand 506 from being pulled out of the nanopore. A blocking group can be any suitable group attached to strand 506, usually at its end, that will prevent the strand from passing through the pore. The blocking group 530 can utilize properties such as size or charge to prevent being pulled through the nanopore. In some cases, blocking group 530 comprises a hairpin region engineered into the end of the strand. The hairpin blocking group is useful for nanopore sequencing as the template nucleic acid can be produced such that the hairpin only forms after the relevant portion of single strand 506 proceeds through the pore, e.g. after releasing a splint oligonucleotide that is bound to strand 506 preventing hairpin formation until it is removed. A blocking group can also be formed by reacting a portion (typically the end) of strand 506 with a specific binding reagent disposed only in the solution below the nanopore.

Once strand 506 is pulled up through the nanopore in step I, it can re-anneal with strand 508 as illustrated by step II and FIG. 5C. Once it is re-annealed, a helicase enzyme 520 (either the same or a different enzyme from 510) can become associated with the re-annealed strands. In some cases, the stringency of the medium can be modified to control the re-annealing process of step II. Sequencing and base modification is then repeated as illustrated by step III and FIG. 5D. The methods shown here allow for obtaining accurate sequencing and modified base detection by repeatedly sequencing the same nucleic acid strand.

In some cases, a second blocking group 540 is used to prevent strand 506 from being pulled through the pore in the direction of sequencing. The blocking group 540 can comprise a hairpin region, a linking between the DNA strands, or a bulky group attached to either strand 506, strand 508, or attached to both strands. In some cases a nucleic acid binding protein, an antibody, or another protein that specifically associates with strand 506 can be used as a blocking group.

In carrying out repeated sequencing with helicase as described herein, hemi-genomic DNA is typically used. The genomic strand can either be strand 506 or strand 508. Also, strand 506 can have either its 3' end or its 5' end extending through the nanopore.

In some cases, repeated sequencing is carried out by combining the polymerase sequencing method of FIG. 1 and the exonuclease sequencing method of FIG. 2. The polymerase and exonuclease activity can derive from separate polymerase and exonuclease enzymes, or the polymerase and exonuclease activity can be in the same enzyme. A number of polymerase enzymes have both a polymerase and 3'-5' exo "proof reading" activity, e.g. phi-29 DNA polymerase. For example, one can start with sequencing using an exonuclease enzyme as shown in FIG. 2. For this method, the translating enzyme may not be attached to the substrate or to the nanopore, but will be held in place by the applied voltage tending to pull strand 206 into the nanopore. The starting nucleotide has a strand 206 that is threaded into the pore using the appropriate voltage. Sequencing and modified base detection are performed while the exonuclease removes nucleotides from strand 208, paying out strand 206 through the pore. A blocking group can be added to the 3' end of strand 206 to prevent the strand 206 from being pulled through the pore. Blocking groups can be any suitable blocking group including those described herein.

After sequencing a portion of strand 206 in this manner, polymerase activity is initiated. Where the enzyme 210 comprises both polymerase activity and exonuclease activity, polymerase activity can be initiated by adding the appropriate reagents for nucleic acid synthesis including nucleotides and cofactors including a catalytic metal such as magnesium or manganese. Where the enzyme 210 only has exonuclease activity, polymerase activity is initiated by exchanging the exonuclease for a polymerase enzyme, and adding the reagents required for nucleic acid synthesis.

Sequencing and modified base detection are then carried out using the polymerase as the translating enzyme as shown in FIG. 1. The polymerase driven sequencing and base modification method pulls the strand 206 (106) back up into the nanopore, and re-synthesizes strand 208 (108). Typically a blocking group as described above is attached to the portion of strand 206 (106) extending through the pore to prevent the strand from being pulled through the pore. When the sequencing and modified base detection are completed in this direction, polymerization activity can be stopped and exonuclease activity initiated to begin sequencing as illustrated in FIG. 2 again. Thus, the same strand is sequenced and its modified bases are identified by kinetics repeatedly providing accurate information. This method has an advantage that the kinetic signatures for the polymerase portion and exonuclease portions will often be different but distinct, allowing for two separate indicators of a given base.

Another approach to repeated sequencing is provided in the method shown in FIG. 3. Because a circular strand 308 is being replicated by polymerase 310, as the enzyme proceeds around and around the circle, the nascent strand 306 will contain the information from strand 308 again and again, and each time, the kinetic signature of the modified bases in strand 308 can be determined. This repeated sequencing provides accurate information for reliably calling out the modified bases in strand 308. This method has the advantage that repeated sequencing and modified base detection is obtained without having to reverse or otherwise change the process. In this method, strand 308 is generally a natural nucleic acid, e.g. genomic DNA, and thus the template nucleic acid comprises a hemi-natural nucleic acid, e.g. hemi-genomic DNA.

FIG. 6 illustrates an exemplary method for repeatedly sequencing and detecting base modification using a polymerase enzyme with strand displacement activity as the translating enzyme and using a circular nucleic acid. A complex is formed between the circular nucleic acid 608 and the polymerase enzyme 610 as illustrated in FIG. 6A. Typically, the complex also comprises a primer. The circular nucleic acid can be, for example, a SMRTBell™ template as described, in U.S. Pat. No. 8,153,375 which is incorporated by reference herein in its entirety for all purposes. In step I, polymerase mediated nucleic acid synthesis is carried out around the circle until it begins to displace the nascent strand 606 shown in FIG. 6B. The complex having the extended nascent strand 606 is then loaded into a nanopore 604 in substrate 602 as shown in step II by applying the appropriate voltage across the nanopore as shown in FIG. 6C. In step III, sequencing and detection of base modification is carried out by adding the reagents for polymerase mediated nucleic acid added, and applying a voltage to hold the polymerase on the nanopore and to provide a force on the strand 606 as shown in FIG. 6D and outlined in FIG. 3.

FIG. 7 illustrates a method of initiating sequencing and modified base detection with a helicase as the translating enzyme. In step I, FIG. 7A, a helicase 710 is mixed with a nucleic acid comprising a strand 708 and strand 706. Strand 706 has an overhanging region that can be used to load the nucleic acid into the nanopore. The helicase forms a complex with the nucleic acid as shown in FIG. 7B. In step II, a solution with the complex is added to substrate 702 having nanopore 704 as shown in FIG. 7C. A voltage is applied across the nanopore to draw strand 706 into the pore. In step III, FIG. 7D, the helicase activity pulls apart the strands 706 and 708, paying out strand 706 through the pore as the voltage applied pulls strand 706 through the pore at a rate controlled by the helicase. In some cases, strand 708 will have engineered into its end region a splint, which when removed will result in the formation of a hairpin 750 at the end of strand 706, providing a blocker useful where repeated sequencing is performed. Typically, a hemi-natural nucleic acid, e.g. hemi-genomic DNA is used in which either strand 706 or strand 708 comprises natural nucleic acid, e.g. genomic DNA.

Template Nucleic Acids

The present invention is generally directed to methods, compositions, and systems for detecting modifications within nucleic acid sequences, for example, methylated nucleotides within sequence templates through the use of single molecule nucleic acid analysis. The ability to detect modifications within nucleic acid sequences is useful for mapping such modifications in various types and/or sets of nucleic acid sequences, e.g., across a set of mRNA transcripts, across a chromosomal region of interest, or across an entire genome. The modifications so mapped can then be related to transcriptional activity, secondary structure of the nucleic acid, siRNA activity, mRNA translation dynamics, kinetics and/or affinities of DNA- and RNA-binding proteins, and other aspects of nucleic acid (e.g., DNA and/or RNA) metabolism.

Although certain embodiments of the invention are described in terms of detection of modified nucleotides or other modifications in a single-stranded DNA molecule (e.g., a single-stranded template DNA), various aspects of the invention are applicable to many different types of nucleic acids, including e.g., single- and double-stranded nucleic acids that may comprise DNA (e.g., genomic DNA, mitochondrial DNA, viral DNA, etc.), RNA (e.g., mRNA, siRNA, microRNA, rRNA, tRNA, snRNA, ribozymes, etc.), RNA-DNA hybrids, PNA, LNA, morpholino, and other RNA and/or DNA hybrids, analogs, mimetics, and derivatives thereof, and combinations of any of the foregoing. Nucleic acids for use with the methods, compositions, and systems provided herein may consist entirely of native nucleotides, or may comprise non-natural bases/nucleotides (e.g., synthetic and/or engineered) that may be paired with native nucleotides or may be paired with the same or a different non-natural base/nucleotide. In certain preferred embodiments, the nucleic acid comprises a combination of single-stranded and double-stranded regions, e.g., such as the templates described in U.S. Ser. Nos. 12/383,855 and 12/413,258, both filed on Mar. 27, 2009 and incorporated herein by reference in their entireties for all purposes. In particular, mRNA modifications are difficult to detect by technologies that require reverse transcriptase PCR amplification because such treatment does not maintain the modification in the amplicons. The present invention provides methods for analyzing modifications in RNA molecules that do not require such amplification. More generally, in certain embodiments, methods are provided that do not require amplification of a modification-containing nucleic acid. In other embodiments, methods are provided for amplification of a modification-containing nucleic acid such that the modifications are maintained in the amplicons.

In many embodiments we have found it is desirable to use a hemi-natural nucleic acid, or hemi-genomic DNA. By hemi-natural, it is meant that one strand has at least portions which comprise natural nucleic acid. The natural nucleic acid can comprise genomic DNA or other natural DNA, or natural RNA including mRNA, rRNA, or tRNA. Natural nucleic acid can have modified bases it is desired to detect. When the natural nucleic acids are amplified, the amplified nucleic acid generally does not contain the modified bases. When fully natural nucleic acids are used, i.e. when both strands are made of natural nucleic acid, there can be modified bases in both of the strands. In some of the methods described herein, for example where using a helicase, modified bases on either strand can cause kinetic changes in the rate of the enzyme activity. When both strands are natural nucleic acid, it can then be difficult to discern which strand has the modified base, complicating the analysis. While in some cases, the kinetic changes from modified bases in the different strands can be discerned, we have found that in many cases it makes analysis more straightforward when hemi-natural nucleic acids such as hemi-genomic DNA are used.

There are many methods of preparing hemi-natural nucleic acids. In general hemi-natural nucleic acids are produced by growing a complementary strand onto a natural nucleic acid strand using the appropriate enzyme. For example, for RNA, a reverse transcriptase can be used to grow a complementary synthetic DNA strand onto the natural RNA creating hemi-natural nucleic acid. DNA polymerases can be used to form complementary synthetic strands onto natural DNA strands to form hemi-natural and hemi-genomic DNA.

Figure 10:
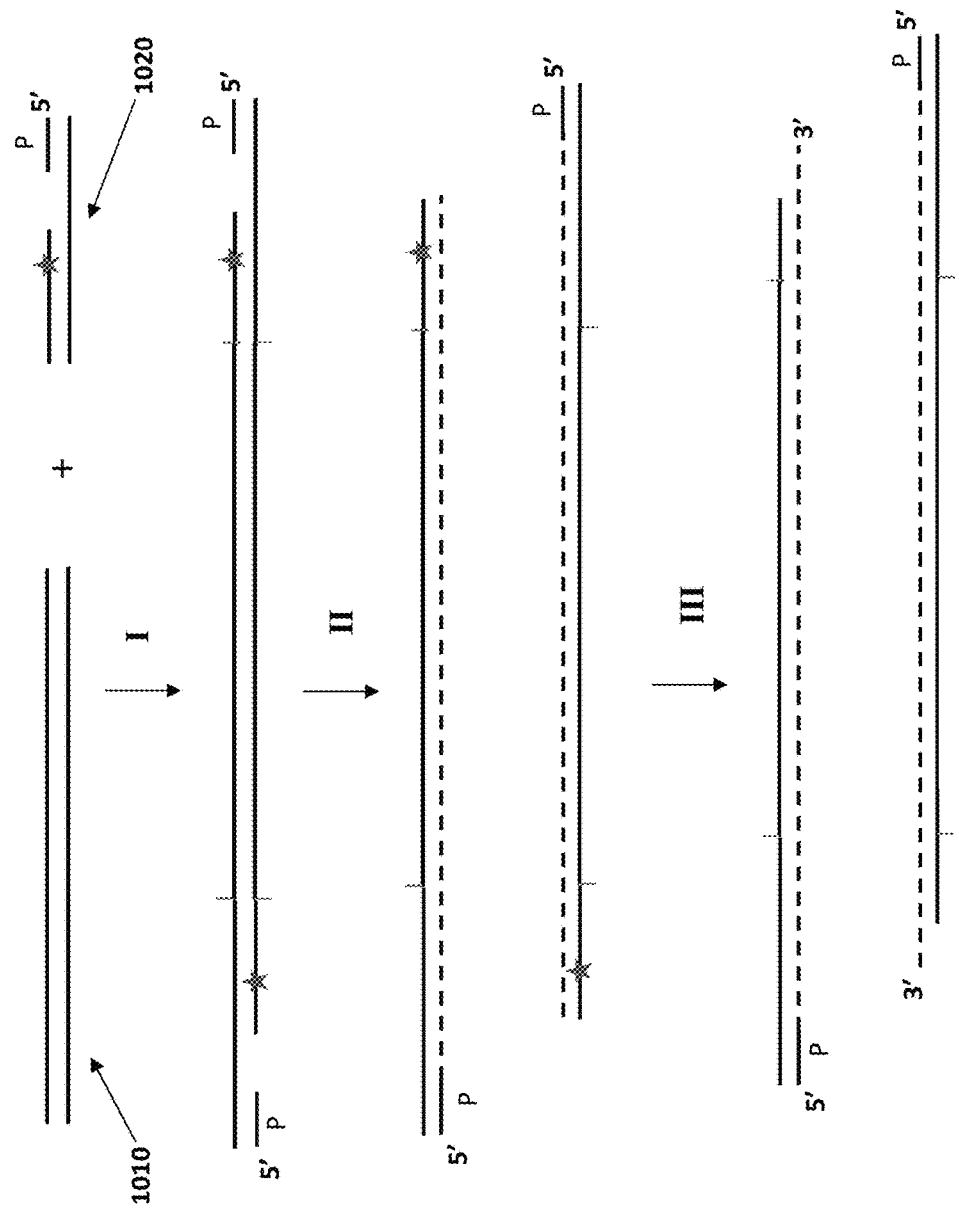
FIG. 10 shows a method for making hemi-natural nucleic acid with a 3' overhang.

For the methods of the instant invention, it can be useful to have hemi-natural nucleic acids with controlled single stranded overhangs at the end for loading into the nanopore. The single stranded overhanging strand can be selectively loaded into the nanopore as described above. FIG. 10 shows an exemplary method of forming a hemi-natural nucleic acid (e.g. hemi-genomic DNA) with an overhanging 3' strand on the synthetic nucleic acid strand. In step I, a double stranded fragment (e.g. genomic DNA) is ligated to an adaptor 1020 having a priming region P and a single-stranded endonuclease (nicking endonuclease) cleavage site (star). In the figure, the adaptor and fragment have blunt ends, and are connected with blunt-end ligation. The ligation can also be done with fragments and adaptors having the appropriate overhangs, e.g. from restriction endonuclease treatment. In step II, a synthetic strand is produced from priming region P using a polymerase enzyme. In step III, a single stranded endonuclease is used to nick the DNA at the single stranded endonuclease cleaving site. It is typically desirable that the nicking endonuclease only cleave one of the strands. This can be accomplished, for example, by using a nicking endonuclease that has a non-palindromic recognition site. Suitable nicking endonucleases are known in the art. Nicking endonucleases are available, for example from New England Biolabs. Suitable nicking endonucleases are also described in Walker, G. T. et al. (1992) Proc. Natl. Acad. Sci. USA, 89, 392-396; Wang, H. and Hays, J. B. (2000) Mol. Biotechnol., 15, 97-104. PMID; Higgins, L. S. et al. (2001) Nucleic Acids Res., 29, 2492-2501; Morgan, R. D. et al. (2000) Biol. Chem., 381, 1123-1125; Xu, Y. et al. (2001) Proc. Natl. Acad. Sci. USA, 98, 12990-12995; Heiter, D. F.

et al. (2005) J. Mol. Biol., 348, 631-40; Samuelson, J. C., Zhu, Z. and Xu, S. Y. (2004) Nucleic Acids Res., 32, 3661-3671; and Zhu, Z. et al. (2004) J. Mol. Biol., 337, 573-583, which are incorporated herein by reference in their entirety for all purposes. In some cases, modified bases can be provided on the adaptor either within the recognition site or opposite the recognition site to direct the nicking endonuclease to cut the desired strand. For example, the endonuclease DpnI which will cut hemimethylated GATC.

The size of the fragment that remains at the 5' end of the natural nucleic acid strand after SSRE cleavage is selected such that it will be released under the conditions of the reaction or with treatment at the appropriate stringency for the oligonucleotide to be released. The resulting hemi-natural nucleic acids have synthetic nucleic acid strands with a 3' overhang. The length of the overhang can be selected for optimizing loading into the nanopore or for other properties. The length of the overhang is typically from about 5 to about 30 bass, but can be from about 1 to about 100 bases or more as desired. In some cases methylated bases are incorporated into the adaptor 1020 in order to control the cleavage of the endonuclease to only the desired strand.

Another methods for producing such hemi-methylated nucleic acids uses portions of RNA in the adaptor which can either be removed to produce a priming site or can be removed to leave an overhang.

Figure 11:
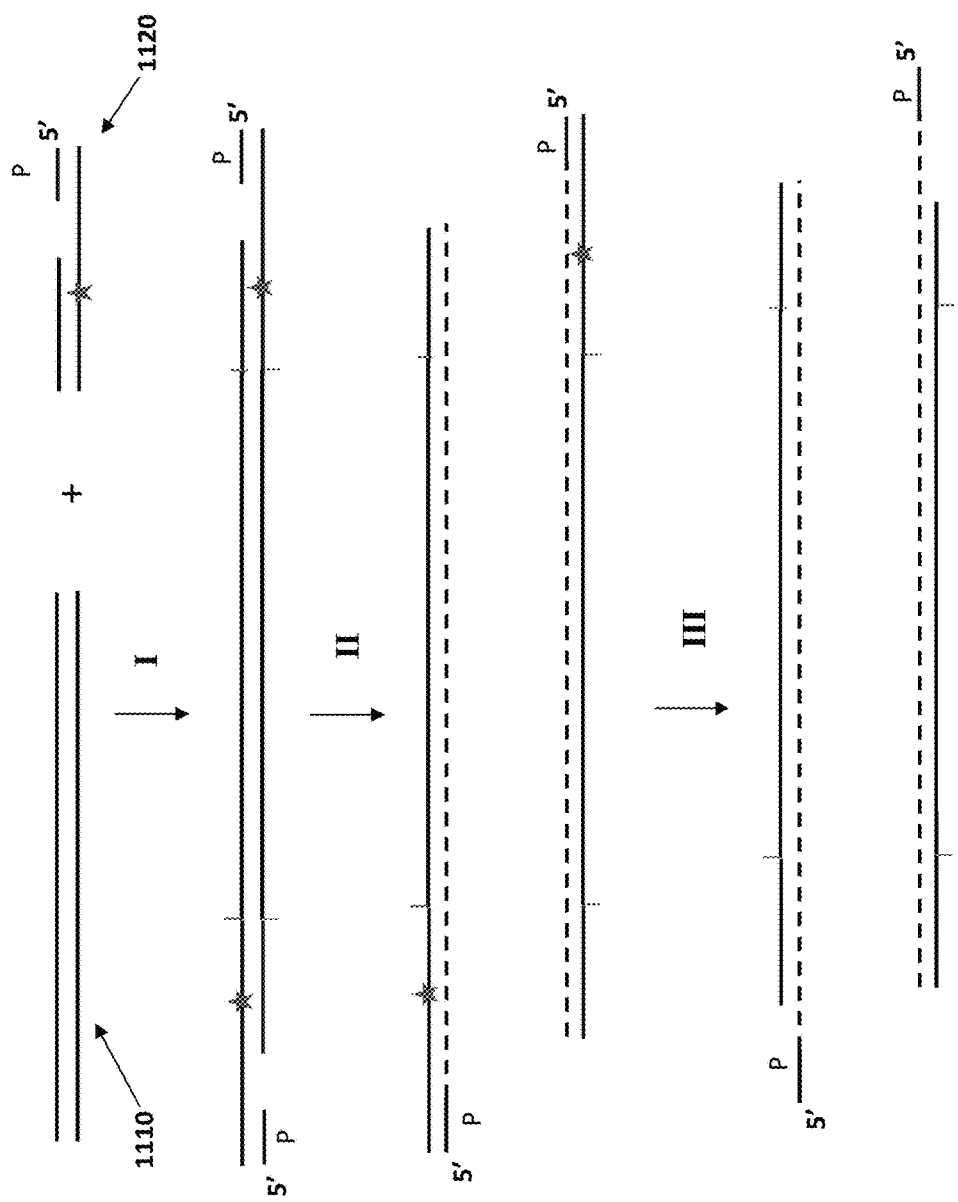
FIG. 11 shows a method for making hemi-natural nucleic acid with a 5' overhang.

FIG. 11 shows an exemplary method of forming a hemi-natural nucleic acid (e.g. hemi-genomic DNA) with an overhanging 5' strand on the synthetic nucleic acid strand. In step I, a double stranded fragment (e.g. genomic DNA) is ligated to an adaptor 1120 having a priming region P and a single-stranded endonuclease (nicking endonuclease) cleavage site (star). In the figure, the adaptor and fragment have blunt ends, and are connected with blunt-end ligation. The ligation can also be done with fragments and adaptors having the appropriate overhangs, e.g. from restriction endonuclease treatment. In step II, a synthetic strand is produced from priming region P using a polymerase enzyme. In step III, a single stranded endonuclease is used to nick the DNA at the single stranded endonuclease cleaving site. The size of the fragment that remains at the 3' end of the natural nucleic acid strand after SSRE cleavage is selected such that it will be released under the conditions of the reaction or with treatment at the appropriate stringency for the oligonucleotide to be released. The resulting hemi-natural nucleic acids have synthetic nucleic acid strands with a 5' overhang. The length of the overhang can be selected for optimizing loading into the nanopore or for other properties. The length of the overhang is typically from about 5 to about 30 bass, but can be from about 1 to about 100 bases or more as desired. In some cases methylated bases are incorporated into the adaptor 1120 in order to control the cleavage of the endonuclease to only the desired strand. For example, a methylated base incorporated into the natural strand can prevent its cleavage while allowing cleavage of the complementary synthetic strand. Analogously, if the SSRE site is on the primer portion, a hemi-natural nucleic acid can be produced in which there is a 3' overhang on the natural (genomic) strand. Other methods for producing such hemi-natural nucleic acids uses portions of RNA in the adaptor which can either be removed to produce a priming site or removed to leave an overhang.

In addition to the adaptors illustrated in FIGS. 10 and 11, FIG. 12 shows some alternative adaptors. FIG. 12A shows an adaptor with a hairpin that can be used, for example to put a hairpin at one end of the double stranded natural nucleic acid fragment. FIG. 12B shows an adaptor that can be used to produce a different overhang region on each strand. FIG. 12C illustrates an adaptor having a primer with a 5' non-hybridized portion that can be used to produce a 5' single stranded overhang for loading into the nanopore. In some cases, hemi-natural nucleic acids can be produced by using the appropriate primer, e.g. a primer having a 5' non-complementary region.

FIG. 13 illustrates that the hemi-natural nucleic acids (hemi-genomic DNA) of the invention can in some cases have a non-complementary region 1370 in addition to the single stranded overhang region 1360 for loading into the nanopore. The non-complementary region 1370 can facilitate the loading of a nucleic acid into the pore, for example when using a helicase enzyme. The length of the segment 1370 is typically from about 1 base to about 12 bases, but can be from about 1 base to about 40 bases. It can be, e.g. 1, 2, 3, 4, 5, 6, 7, 8, 9, 10, 11, or 12 bases in length.

To facilitate repeat reading of the molecules, a blocking group or stopper moiety can be employed at one end to prevent the molecule from passing all the way through. This stopper can be attached to a fragment of genomic DNA using a variety of methods. One convenient method is to ligate universal adapters to one end of the molecule, said universal adapter being synthesized with a bulky side group. Methods are known in the art for attaching such side groups to either 3' or 5' DNA ends, or at positions interior to such an adapter sequence. These side groups can be attached covalently or non-covalently such as through the streptavidin-biotin interaction. The blocking group can be a hairpin of DNA with a self-complementary section that creates a section of double stranded DNA that will not pass through the nanopore. To allow blocking of both ends, means can be employed to cause a plug to form after the DNA molecule has threaded the nanopore. For example, universal adapters and ligase enzymes can be provided on the trans side of the nanopore solution so that once the molecule has threaded it is available for ligation. In one implementation a first universal adapter would be ligated to the "insertion end" of the DNA prior to application of the DNA to the nanopore. This sequence would allow a hybridization of a reverse-complement oligonucleotide to bind on the trans side. This double stranded region would serve as a stopper. This stopper would have the merit of being reversible in that a larger voltage can be applied and strip off the reverse complement oligonucleotide, allowing the pore to be re-used on a different DNA strand.

In another implementation, the universal adapter is used to allow targeted ligation of another strand. In this method, there is a splint oligo, and a ligation oligo that contains a blocking function (using any of the aforementioned blocking elements, including a hairpin sequence). The splint has a region that is complementary to the adapter on the trans-end of the DNA molecule and a region that is complementary to one end of the blocking oligo. The sequences are chosen such that the three elements form an appropriate substrate for one of the many DNA ligases. A ligase enzyme binds the site and joins the blocking oligo covalently with the trans end of the DNA strand.

Figure 8A:
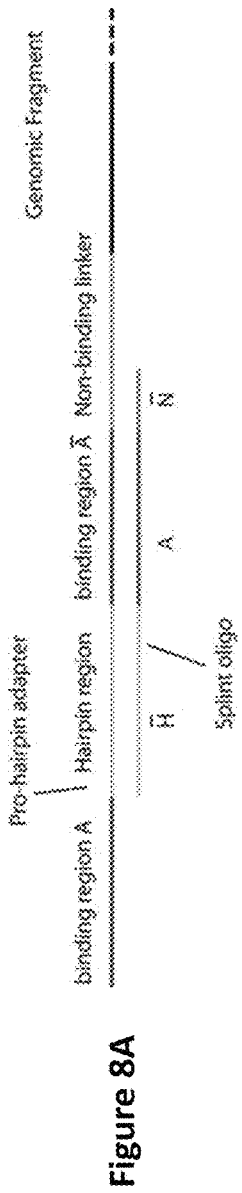
FIGS. 8A and 8B illustrate using a splint oligo to deliver a hairpin blocker into a nanopore.
Figure 8B:
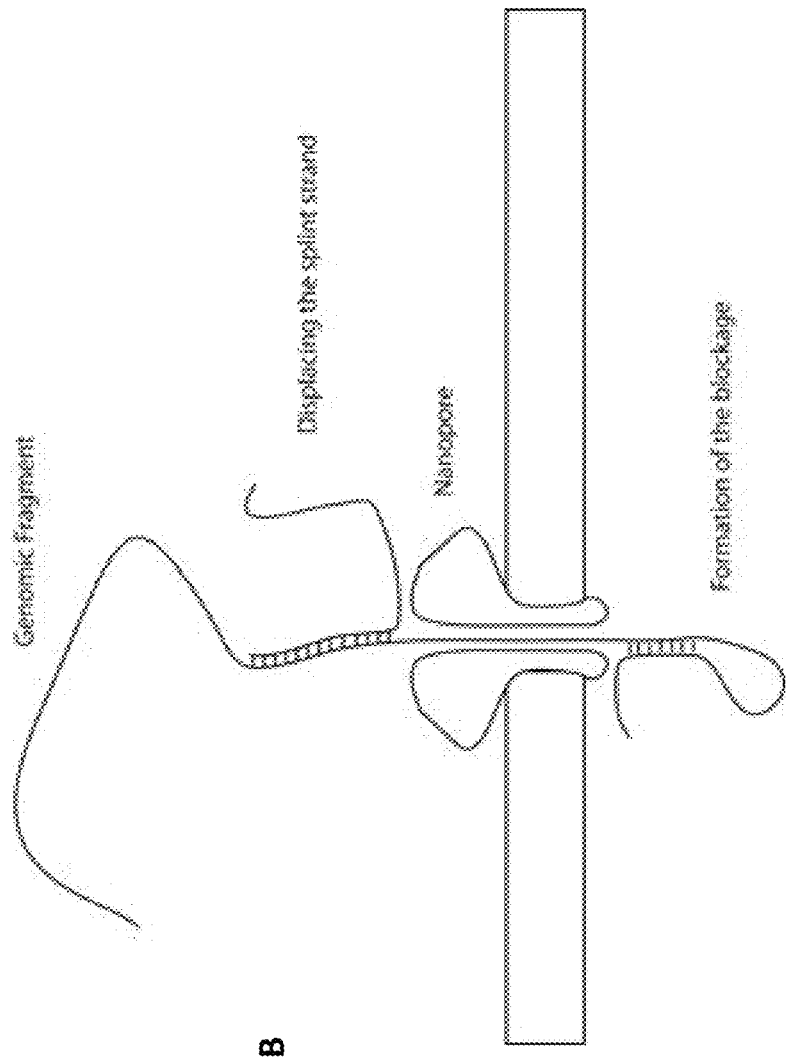

Another implementation allows that the trans-end blocker is triggered to form by the passage of the DNA through the pore. One implementation of this is to provide a hairpin sequence at the trans end that is held open by a splint oligo that leaves a small number of bases overhanging at the trans end to allow for insertion into the pore. The splint molecule would hybridize with the other half of the hairpin sequence, so the free end would not close into a hairpin. However, when the molecule is inserted into a nanopore, a strand-displacing voltage (known to those skilled in the art) is applied, the splint will be stripped off, and the normal hairpin structure will spontaneously form on the trans side of the pore, creating the blocking function. FIG. 8(A) shows an example of the structure of a template nucleic acid having a splint strand hybridized so as to prevent formation of the hairpin structure until its removal. FIG. 8(B) shows how the hairpin forms on one side of the nanopore after the splint strand has been displaced, forming a blockage.

In some aspects, the invention provides a nucleic acid template molecule for use in nanopore sequencing comprising: a partially double-stranded nucleic acid comprising a sample strand comprising a nucleic acid sequence of interest connected to an adaptor comprising a binding region A', a hairpin region H, and a binding region A that is complementary to binding region A, and a splint oligonucleotide strand hybridized to the sample strand comprising an H' region complementary to the hairpin region H, and a region A, complementary to binding region A' of the sample strand, whereby, when the splint oligonucleotides is removed from the sample strand, a hairpin region can be formed in the sample strand by the hybridization of binding regions A and A'.

In some embodiments the nucleic acid template further comprising a non-binding linker sequence N between binding region A' and the sequence of interest. In addition, the nucleotide can further comprising a sequence N' in the splint oligonucleotide complementary to at least a portion of the non-binding linker sequence N.

In some aspects, the invention provides sequencing with hemi-natural nucleic acids (e.g. hemi-genomic DNA) wherein a natural strand and a synthetic strand are connected such that the same pore sequences both the natural and synthetic strand. This can be accomplished, for example, by having a hairpin adaptor that connects these strands at one end. By having the same pore provide sequence information about both a natural sequence (including modified bases), and a synthetic sequence that does not have modified bases, one can gain more confidence about the identity and position of the modified base. As described herein, kinetic information, current blockage information, or a combination of both can be used to identify a modified base with nanopore sequencing. Providing a single pore with stretches of natural sequence and synthetic sequence, where the natural and synthetic sequence are the same or complementary, allows for using information from the non-modified synthetic sequence to better identify a modified base within the natural sequence. For example a pore will typically show different characteristics for different sequence contexts. When analyzing a natural strand which may or may not have a modified base, the presence of the modified base may change the current blockade characteristics in a manner that could be interpreted as indicative of a different sequence context. By independently sequencing the same or a complementary sequence in the same pore on the same nucleic acid strand in a portion where there are no modifications, the user is able to verify that the change in blockade current by the modified base is indeed due to the modified base since the sequence context is independently determined.

The hemi-natural nucleic acid used for this type of analysis will typically have a strand having a natural sequence with a complementary sequence connected to it either directly or through a connecting sequence of nucleic acid. In some cases, the template can comprise a double-stranded nucleic acid, one strand natural nucleic acid and the other strand synthetic nucleic acid, and having a hairpin at one end. This type of construct can comprise DNA or RNA or a combination of DNA and RNA. The natural sequence can comprise either the strand that is 3' of the synthetic sequence, or the strand that is 5' of the synthetic sequence. In some cases, the template includes a synthetic sequence that is substantially identical to the natural sequence. For example, the template can be 3'-natural sequence-connecting sequence-synthetic complementary sequence-connecting sequence-substantially identical sequence-5'. Alternatively the template can be 5'-natural sequence-connecting sequence-synthetic complementary sequence-connecting sequence-substantially identical sequence-3'. In other cases the template will not have regions of complementary sequence and will be 3'-natural sequence-connecting sequence-substantially identical sequence-5' or 5'-natural sequence-connecting sequence-substantially identical sequence-3'.

FIG. 14 shows representative structures for the hemi-natural nucleic acid (e.g. hemi-genomic DNA) templates of the invention. FIG. 14A shows a template with a natural sequence, a complementary sequence, and a hairpin nucleic acid connecting the sequences. The natural sequence is 3' of the synthetic sequence and there is an overhang at the 3' end. As described herein, it can be useful for the templates to have either a 3' or a 5' overhang in order to effectively thread the template into the nanopore in a single stranded manner FIG. 14B shows a template with natural sequence and a synthetic sequence complementary to the natural sequence with a hairpin nucleotide connecting the two. The natural sequence is 5' of the synthetic sequence, and the template has a 5' overhang. FIG. 14C shows a template having a natural sequence and a synthetic sequence connected by a hairpin nucleic acid with the natural sequence 3' of the synthetic sequence, and a 5' overhang. FIG. 14D shows a template having a natural sequence and a complementary synthetic sequence connected by a hairpin nucleic acid.

FIG. 14E shows a template nucleic acid with a natural sequence and a synthetic sequence 1410 connected by a connecting nucleic acid in one strand, with a complementary synthetic strand 1412 hybridized to it. The synthetic sequence 1410 can be complementary to the natural sequence or substantially similar to the natural strand. The natural sequence is 3' of the synthetic sequence 1410 and there is a 5' overhang. FIG. 14F shows a template nucleic acid having a natural sequence 1428 and a synthetic sequence 1420 on the same strand connected by a connecting nucleic acid 1426. There is a synthetic section 1422 that is complementary and hybridized to the natural sequence 1428, connector sequence 1426 and synthetic sequence 1422. The synthetic portion 1422 is connected to these sequences by hairpin loop 1424. The natural sequence is 3' of synthetic sequence 1420, and the template has a 5' overhang. FIG. 14G shows a template nucleic acid with a natural sequence 1438 connected through a connector nucleic acid 1436 to synthetic sequence 1430. A hairpin nucleic acid 1434 connects this set of sequences to synthetic portion 1432 that is complementary to and hybridized to the set of sequences. The natural sequence is 3' of the synthetic sequence 1430 and the template has a 3' overhang. Synthetic sequences 1420 and 1430 can either be complementary or substantially identical to their corresponding natural sequences 1428 and 1438. The structures shown here are not meant to be limiting, and one of skill will understand that the hemi-natural templates of the invention encompass many other related structures.

A template of the invention that can be particularly advantageous is a temple that has a natural sequence, and a synthetic sequence that is substantially identical to it. In some cases, the natural sequence and the synthetic sequence have between them a sequence that is complementary to the natural sequence. FIG. 15 shows an exemplary approach for obtaining such templates. FIG. 15A shows a method for obtaining a template for nanopore sequencing having a natural sequence and a synthetic sequence that are substantially identical with a complementary synthetic sequence between these sequences. FIG. 15B shows a method for obtaining a template for nanopore sequencing having a natural sequence and a synthetic sequence that are substantially identical with a complementary natural sequence between these sequences.

The method in FIG. 15A begins with a double stranded nucleic acid sample having one strand with synthetic sequence 1504 and one strand with natural sequence 1502. This sample can be, for example messenger RNA as the natural strand, and a synthesized complementary DNA strand. The sample could also be double stranded DNA with one genomic strand and a synthetic complementary strand. In the method shown, there are overhangs on each end of the double stranded portion. In some cases, blunt ended samples can also be used. In step (I) a hairpin 1510 is added to one end of the double stranded nucleic acid. The hairpin can have a stop region (designated by the star) which halts polymerase synthesis at that point. Such stop regions are well known in the art, and could be an abasic site, a sequence indicating to the enzyme to stop, or a nucleotide that it modified to prevent further synthesis. Stop regions are described, for example, in US 2012-0322692 which is incorporated herein by reference for all purposes. In some cases, the double stranded nucleic acid having a hairpin at one end is made in a single step, e.g. by having a unique overlap site at one end of the double stranded sample. In some cases, the double stranded nucleic acid having a hairpin at one end is made in a process whereby first, a construct having hairpins at both ends is produced, followed by cleaving the hairpin selectively from one end, e.g. with a restriction enzyme. In step (II) hairpin structure 1520 is added to the free end of the double stranded region. The hairpin structure 1520 has a gap in the sequence on one side of the hairpin to act as a priming site.

In step (III) a polymerase enzyme with strand displacement activity 1530 is added under conditions conducive to nucleic acid synthesis. The polymerase synthesizes a strand with sequence 1540 complementary to sequence 1504, and displacing the strand with sequence 1502. In step (IV), the polymerase enzyme meets the stop region, halting nucleic acid synthesis. The result of this process is a template molecule that can be used for nanopore sequencing and modified base detection that has a natural sequence 1502, a complementary synthetic sequence 1504, and a synthetic sequence 1540 that is substantially identical to the natural strand 1502.

The method in FIG. 15B begins with a double stranded nucleic acid sample having two strands with natural sequences 1506 and 1508. This sample can be, for example, a double stranded fragment of genomic DNA. In the method shown, there are overhangs on each end of the double stranded portion. In some cases, blunt ended samples can also be used. In step (I) a hairpin 1512 is added to one end of the double stranded nucleic acid. The hairpin can have a stop region (designated by the star) which halts polymerase synthesis at that point. Such stop regions are well known in the art, and could be an abasic site, a sequence indicating to the enzyme to stop, or a nucleotide that it modified to prevent further synthesis. Stop regions are described, for example, in US 2012-0322692 which is incorporated herein by reference for all purposes. In some cases, the double stranded nucleic acid having a hairpin at one end is made in a single step, e.g. by having a unique overlap site at one end of the double stranded sample. In some cases, the double stranded nucleic acid having a hairpin at one end is made in a process whereby first, a construct having hairpins at both ends is produced, followed by cleaving the hairpin selectively from one end, e.g. with a restriction enzyme. In step (II) hairpin structure 1522 is added to the free end of the double stranded region. The hairpin structure 1522 has a gap in the sequence on one side of the hairpin to act as a priming site.

In step (III) a polymerase enzyme with strand displacement activity 1532 is added under conditions conducive to nucleic acid synthesis. The polymerase synthesizes a strand having sequence 1542 complementary to sequence 1508, and displacing the strand with sequence 1506. In step (IV), the polymerase enzyme meets the stop region, halting nucleic acid synthesis. The result of this process is a template molecule that can be used for nanopore sequencing and modified base detection that has a natural sequence 1506, a complementary natural sequence 1508, and a synthetic sequence 1542 that is substantially identical to the natural strand 1506.

The hemi-natural templates described herein can have a blocking group or hairpin locking group as described herein to allow for repeated sequencing of the same molecule with a nanopore.

An advantage to having both a natural and synthetic version of the same sequence or its compliment is that the natural sequence will be the sequence that may have modified bases. In some cases, as described herein, the modified base will alter the signal from the passage of that base through the pore. The user will then have to determine whether the observed change in signal is due to a modified base or due to a different sequence context. A synthetic version of the same signal will typically have no modified bases, thus, the signal from the synthetic sequence can be used for comparison to verify that a change in signal is indeed due to the presence of a modified base. Since modified and unmodified versions of the same sequence are read in the same pore, systematic errors can be minimized Having a natural sequence and a complementary synthetic sequence in the same template can have similar advantage in improving sequence quality. Unlike a synthetic version of the same sequence, a synthetic version of a complementary sequence will not exhibit the same sequence as an unmodified version of the natural sequence. However, since the complementary sequence is known to be unmodified, its sequence can typically be determined more reliably than for the modified natural sequence. First the complementary synthetic sequence is determined, then in-silico, a signal profile for the complement of that sequence can be determined. The signal profile determined in-silico can be used to validate the presence of modified bases by providing an expected signal for the non-modified version.

Thus when a natural sequence and a synthetic sequence essentially identical to the natural sequence is sequenced in the same molecule, we can compare signals form natural Crick strand with a synthetic Crick strand. When a natural sequence and a synthetic complement to the natural sequence are sequenced, we have a signal for a natural Crick strand, we use signal from a synthetic Watson strand to produce in-silico a signal corresponding to the synthetic Crick strand. Thus we are comparing signal from a natural Crick strand with an in-silico signal from an Crick strand. These approaches can be combined, for example, when sequencing templates shown in FIG. 15 having both synthetic and natural versions of the same sequence that could be sequenced multiple times.

The phrase "substantially identical," in the context of two nucleic acids refers to two or more sequences or subsequences that have at least about 80%, about 90%, about 95%, about 98%, about 99% or more nucleotide identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared. Methods for determining sequence similarity percentages (e.g., BLASTP and BLASTN using default parameters) are described herein and are generally available.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2012).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information In addition to calculating percent sequence identity, the BLAST algorithm also performs a statistical analysis of the similarity between two sequences (see, e.g., Karlin & Altschul (1993) Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Sequencing and Modified Base Identification

The invention provides both sequence information and modified base identification. Methods for determining sequencing using nanopores are well known. See e.g., Nature Biology, doi:10.1038/nbt.2171, WO2011067559, EP1951898, U.S. Pat. Nos. 6,673,615, 6,362,002, and 5,795,782, which are incorporated herein by reference in their entirety for all purposes. In some cases, the modified bases can be called out using the electrical characteristics when the modified bases pass through the nanopore (see e.g. Mirsaidov, U. et al. Nanoelectromechanics of methylated DNA in a synthetic nanopore. Biophys. J. 96, L32-L34 (2009); Wanunu, M. et al. Discrimination of methylcytosine from hydroxymethylcytosine in DNA molecules. J. Am. Chem. Soc. 133, 486-492 (2010), which are incorporated herein by reference in their entirety for all purposes). We have found that one can use the kinetic information from nanopore sequencing using a translating enzyme in order to more reliably call the modified bases.

One kinetic parameter that is used in the invention is the inter-transition distance, or IDT. When carrying out nanopore sequencing one typically identifies transitions in the current passing through the nanopore that correspond to the a movement from one portion of the strand to the next (e.g. the translation of one base unit). These transitions can represent distinct sharp transitions between plateaus of current levels. These transitions can be correlated with one-base movement of the single stranded nucleic acid in the nanopore. See, e.g. Manrao et al. Nature Biotechnology, doi: 10.1038/nbt.2171 which is incorporated herein by reference in its entirety for all purposes. Thus, the length of a plateau, the distance between transitions provides a measure of the rate of the transport of the nucleic acid through the pore. Since in accordance with the instant methods, the voltage is controlled such that the rate of translation through the pore is substantially the same as the rate of the translating enzyme, the ITD provides a measure of the kinetics of the enzyme. In addition to the measurement of current through the nanopore other electrical signals can be detected including capacitance, and electron tunneling current.

There are other parameters that can be used in addition to ITD in order to measure the translating enzyme kinetics and thereby call identify the modified base. In some cases, the oscillations in the current during the transit of a base can be used for base identification. The oscillation in current can occur for various reasons. In some cases, a nucleotide within the pore can oscillate due to Brownian motion between the two states, leading to fluctuations in the conductance of the nanopore. This oscillation is manifested as a variation of the blockade current over time. This variation can produce a magnitude and frequency spectrum. Nucleotides or analogs that can thus be identified by either or both of the magnitude of the current blockage and the spectrum of the electrical oscillation they produce. Voltage level discrimination and oscillation discrimination can be used in conjunction to increase the resolution of the system. In some cases, oscillations look like noise, but noise with reproducible and identifiable characteristics including the frequency and the magnitude of the signal. These different types of noise can be used like different colored dyes are used to differentiate between different nucleotide analogs, thus, we refer herein to a distinguishable type of noise as a noise color. While the measurement of current blockage by the blockade label is described as a measurement of current, it is understood by those in the art that this current can be measured by measuring a voltage. Where we refer to measuring current or voltage, it is to be understood that one can be used to measure or represent the other with respect to measuring ion flow through the nanopore. In addition to current and voltage, resistance or impedance measurements can also be employed as described in more detail herein to measure the level of current through the nanopore while the nucleotide passes through.

One aspect of the invention is the utilization of additional parameters beyond just the amplitude of a signal to classify the species that inside a nanopore. Such parameters are measurable over the duration of the time between electronic transitions indicating the presence of bases. Two general categories of measurement scenarios are: quasi-equilibrium measurement and non-equilibrium measurement.

In quasi-equilibrium measurement, there is some static constraint that remains in place over the duration of the event, and the removal of that constraint effectively determines the end of the event (except for a negligibly short interval at the end while the detectable object clears the nanopore). Though the constraint is fixed, the rest of the components of the system are free to move, and this leads to fluctuations in the signal. For example, diffusion (or equivalently Brownian motion) will cause movement of the nucleotide. Under most circumstances, that motion will be correlated with changes in the current across the nanopore, and thus the voltages that might be measured elsewhere in the system. Because of this, aspects of the detectable moiety such as the submolecular diffusion constant (the diffusibility of just that part of the molecule, even when another part of the molecule is constrained) will change the speed of those motions and thus the characteristic frequencies with which the observed voltages or currents will change. For example, a fast diffuser will generally have a whiter noise spectrum, while a slower diffuser will tend to produce a pinker noise spectrum.

The noise color can be used as the basis for a discriminator, for example, by 1) taking the noise signature over a region of interest (e.g. over the duration of the event), 2) performing a Fourier transform analysis, or an autocorrelation analysis and examine the spectrum of the noise over the range of frequencies available (e.g. from $f=1/T$ where T is the duration of a pulse, up to the cutoff frequency of the amplifier system, or somewhat beyond the cutoff). This process results in a digitally sampled noise amplitude as a function of frequency. This could be represented by as few as two samples (a low frequency region and a high frequency region), 3, 4, 5, 6, 7, 8, 9, 10, 11, 12, 16, 32, 64, 128, 256, 512, 1024 or more bins. The values in these bins could be discrete samples of a function or they represent integrals over a region of interest of the idealized continuous function. This set of discrete values can be represented as a vector that can be classified by one of many machine learning systems such as k-means clustering, SVM, CART or boosted CART, PCA and many others. Thus, as described herein, noise color can be used to discriminate detectable moieties. Detection systems that are based on noise color can be referred to as "noise-color identification systems".

Nanopores

As used herein the term nanopore, nanometer scale aperture, and nanoscale aperture are used interchangeably. In each case, the term generally refers to an opening which is of a size such that when molecules of interest pass through the opening, the passage of the molecules can be detected by a change in signal, for example, electrical signal, e.g. current. In some cases the nanopore comprises a protein, such as alpha-hemolysin or MspA, which can be modified or unmodified. In some cases, the nanopore is disposed within a membrane, or lipid bilayer, which can be attached to the surface of the microfluidic region of the device of the invention by using surface treatments as described herein and as known in the art.

In some cases, the nanopore can be a solid state nanopore. Solid state nanopores can be produced as described in U.S. Pat. Nos. 7,258,838, 7,504,058 In some cases the nanopore comprises a hybrid protein/solid state nanopore in which a nanopore protein is incorporated into a solid state nanopore. Suitable nanopores are described, for example in Mager, M. D. & Melosh, N. A. Nanopore-spanning lipid bilayers for controlled chemical release. *Adv. Mater.* 20, 4423-4427 (2008); White, R. J. et al. Ionic conductivity of the aqueous layer separating a lipid bilayer membrane and a glass support. *Langmuir* 22, 10777-10783 (2006); Venkatesan, B. M. et al. Lipid bilayer coated $Al_2O_3$ nanopore sensors: towards a hybrid biological solid-state nanopore. *Biomed. Microdevices* 13, 671-682 (2011) which are incorporated herein by reference in their entirety for all purposes. Suitable solid state nanopores are describe in: Storm, A. J., Chen, J. H., Ling, X. S., Zandbergen, H. W. & Dekker, C. Fabrication of solid-state nanopores with single nanometre precision, Nature Mater. 2, 537-540 (2003); Venkatesan, B. M. et al. Highly sensitive, mechanically stable nanopore sensors for DNA analysis. Adv. Mater. 21, 2771-2776 (2009); Kim, M. J., Wanunu, M., Bell, D. C. & Meller, A. Rapid fabrication of uniformly sized nanopores and nanopore arrays for parallel DNA analysis. Adv. Mater. 18, 3149-3153 (2006); Nam, S-W., Rooks, M. J., Kim, K-B. & Rossnagel, S. M. Ionic field effect transistors with sub-10 nm multiple nanopores. Nano Lett. 9, 2044-2048 (2009) and Healy, K., Schiedt, B. & Morrison, A. P. Solid-state nanopore technologies for nanopore-based DNA analysis. Nanomedicine 2, 875-897 (2007) which are incorporated herein by reference in their entirety for all purposes.

In some cases, graphene can be used, as described in: Geim, A. K. Graphene: status and prospects. Science 324, 1530-1534 (2009); Fischbein, M. D. & Drndic, M. Electron beam nanosculpting of suspended graphene sheets. Appl. Phys. Lett. 93, 113107-113103 (2008); Girit, Ç. Ö. et al. Graphene at the edge: stability and dynamics. Science 323, 1705-1708 (2009); Garaj, S. et al. Graphene as a subnanometre trans-electrode membrane. Nature 467, 190-193 (2010); 52. Merchant, C. A. et al. DNA translocation through graphene nanopores. Nano Lett. 10, 2915-2921 (2010); Schneider, G. F. et al. DNA translocation through graphene nanopores. Nano Lett. 10, 3163-3167 (2010); Hall, J. E. Access resistance of a small circular pore. J. Gen. Physiol 66, 531-532 (1975); and Song, B. et al. Atomic-scale electron-beam sculpting of near-defect-free graphene nanostructures. Nano Lett. 11, 2247-2250 (2011) which are incorporated herein by reference in their entirety for all purposes.

Preferred nanopore structures include hybrid nanopores as described, for example, in US20100331194; Iqbal, S. M., Akin, D. & Bashir, R. Solid-state nanopore channels with DNA selectivity. Nature Nanotech. 2, 243-248 (2007); Wanunu, M. & Meller, A. Chemically modified solid-state nanopores. Nano Lett. 7, 1580-1585 (2007); Siwy, Z. S. & Howorka, S. Engineered voltage-responsive nanopores. Chem. Soc. Rev. 39, 1115-1132 (2009); Kowalczyk, S. W. et al. Single-molecule transport across an individual biomimetic nuclear pore complex. Nature Nanotech. 6, 433-438 (2011); Yusko, E. C. et al. Controlling protein translocation through nanopores with bio-inspired fluid walls. Nature Nanotech. 6, 253-260 (2011); and Hall, A. R. et al. Hybrid pore formation by directed insertion of alpha-haemolysin into solid-state nanopores. Nature Nanotech. 5, 874-877 (2010) which are incorporated herein by reference in their entirety for all purposes.

In the instant invention, the translating enzyme should be fixed in space during the sequencing reaction to ensure that the distance between the base modification event at the enzyme and the bases in the nanopore remains constant. In some cases the enzyme is attached proximal to the nanopore. The attachment can be covalent, by affinity, or through genetic fusion with a biological nanopore. See e.g. US20110174625, US20110229877, WO2010086603, and U.S. Pat. No. 6,746,594 which are incorporated herein by reference in their entirety for all purposes. Alternatively the translating enzyme can be held in place with the voltage across the nanopore that is used to pull the nucleic acid into the pore. The translating enzyme forms a complex with the nucleic acid at the site of enzyme activity. In accordance with the invention, the voltage is applied such that the enzyme is drawn toward the pore, and is held in place sterically. The voltage provides a constant force, pulling the nucleotide into the pore, and the enzyme either pays out the nucleic acid through the pore in the direction of the force, or pulls the nucleic acid into the pore against the field as described herein.

Kinetic Signatures

Generally speaking, the methods of the invention involve monitoring of an analytical reaction to collect "reaction data," wherein the reaction data is indicative of the progress of the reaction. Reaction data includes data collected directly from the reaction, as well as the results of various manipulations of that directly collected data, any or a combination of which can serve as a signal for the presence of a modification in the template nucleic acid. Reaction data gathered during a reaction is analyzed to identify characteristics indicative of the presence of a modification, and typically such data comprises changes or perturbations relative to data generated in the absence of the modification. For example, certain types of reaction data are collected in real time during the course of the reaction, such as metrics related to reaction kinetics, affinity, rate, processivity, signal characteristics, and the like. As used herein, "kinetics," "kinetic signature," "kinetic response," "activity," and "behavior" of an enzyme (or other reaction component, or the reaction as a whole) generally refer to reaction data related to the function/progress of the enzyme (or component or reaction) under investigation and are often used interchangeably herein. Signal characteristics vary depending on the type of analytical reaction being monitored. For example, some reactions use detectable labels to tag one or more reaction components, and signal characteristics for a detectable label include, but are not limited to, the type of signal (e.g., wavelength, charge, etc.) and the shape of the signal (e.g., height, width, curve, etc.). Further, signal characteristics for multiple signals (e.g., temporally adjacent signals) can also be used, including, e.g., the distance between signals during a reaction, the number and/or kinetics of extra signals (e.g., that do not correspond to the progress of the reaction, such as cognate or non-cognate sampling), internal complementarity, and the local signal context (i.e., one or more signal that precede and/or follow a given signal). For example, template-directed sequencing reactions often combine signal data from multiple nucleotide incorporation events to generate a sequence read for a nascent strand synthesized, and this sequence read is used to derive, e.g., by complementarity, the sequence of the template strand. Other types of reaction data are generated from statistical analysis of real time reaction data, including, e.g., accuracy, precision, conformance, etc. In some embodiments, data from a source other than the reaction being monitored is also used. For example, a sequence read generated during a nucleic acid sequencing reaction can be compared to sequence reads generated in replicate experiments, or to known or derived reference sequences from the same or a related biological source. Alternatively or additionally, a portion of a template nucleic acid preparation can be amplified using unmodified nucleotides and subsequently sequenced to provide an experimental reference sequence to be compared to the sequence of the original template in the absence of amplification. Although certain specific embodiments of the use of particular types of reaction data to detect certain kinds of modifications are described at length herein, it is to be understood that the methods, compositions, and systems are not limited to these specific embodiments. Different types of reaction data can be combined to detect various kinds of modifications, and in certain embodiments more than one type of modification can be detected and identified during a single reaction on a single template. Such variations to the detailed embodiments of the invention will be clear to one of ordinary skill based upon the teachings provided herein.

Modified Bases

Figure 9:
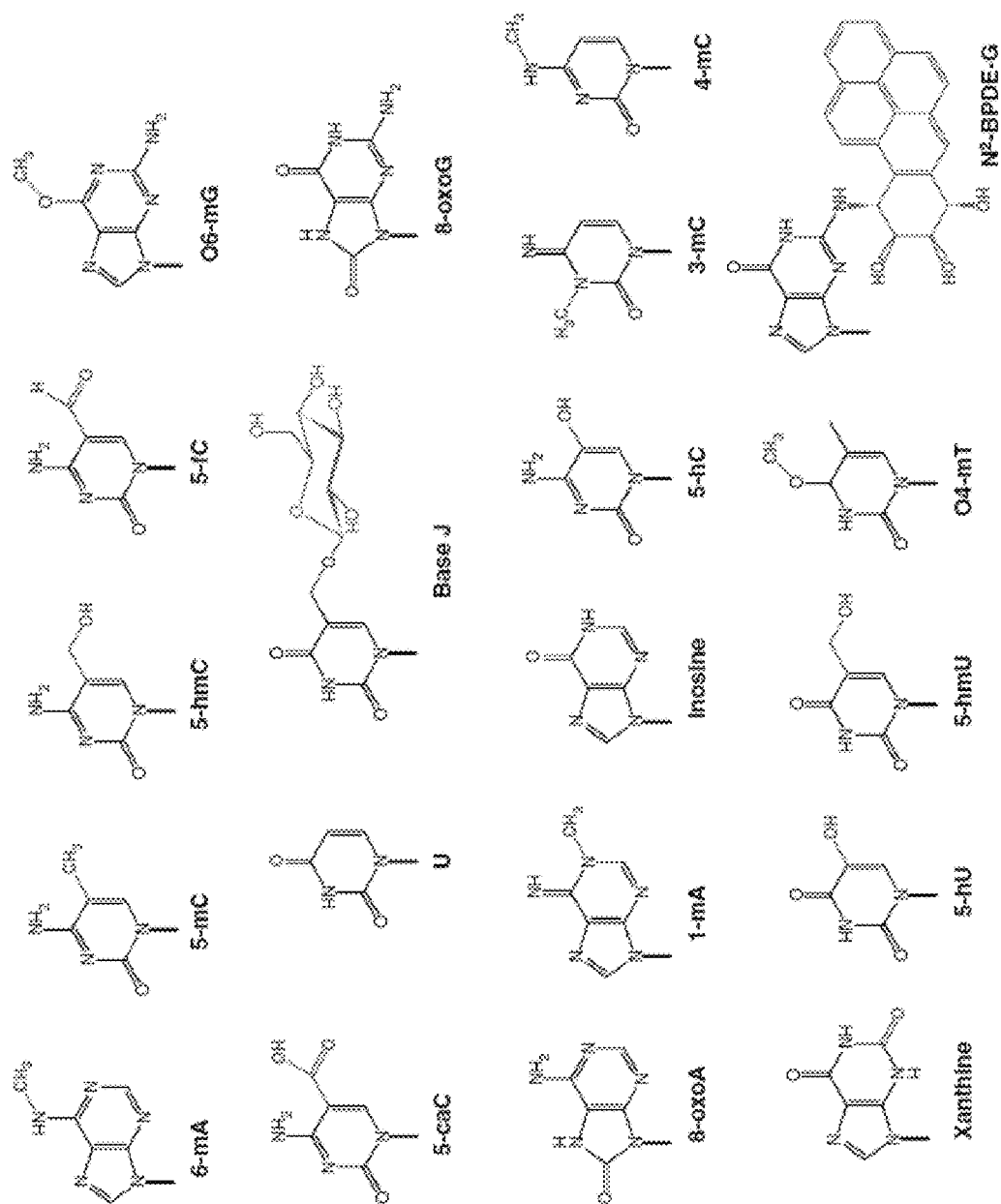
FIG. 9 shows some representative modified bases.

The modified bases that can be detected by kinetics as described herein include any suitable base that differs from the canonical bases A, C, G, T, or A, C, G, U. There are different modified bases in different types of organisms, e.g. prokaryotes and eukaryotes that are used for example to control DNA replication and expression. There are also many types of modified bases that result from environmental damage to the DNA and RNA in the body. Examples of suitable modified bases are provided in FIG. 9.

The term "modification" as used herein is intended to refer not only to a chemical modification of a nucleic acids, but also to a variation in nucleic acid conformation or composition, interaction of an agent with a nucleic acid (e.g., bound to the nucleic acid), and other perturbations associated with the nucleic acid. As such, a location or position of a modification is a locus (e.g., a single nucleotide or multiple contiguous or noncontiguous nucleotides) at which such modification occurs within the nucleic acid. For a double-stranded template, such a modification may occur in the strand complementary to a nascent strand synthesized by a polymerase processing the template, or may occur in the displaced strand. Although certain specific embodiments of the invention are described in terms of 5-methylcytosine detection, detection of other types of modified nucleotides (e.g., $N^6$-methyladenosine, $N^3$-methyladenosine, $N^7$-methylguanosine, 5-hydroxymethylcytosine, other methylated nucleotides, pseudouridine, thiouridine, isoguanosine, isocytosine, dihydrouridine, queuosine, wyosine, inosine, triazole, diaminopurine, β-D-glucopyranosyloxymethyluracil (a.k.a., β-D-glucosyl-HOMedU, β-glucosyl-hydroxymethyluracil, "dJ," or "base J"), 8-oxoguanosine, and 2'-O-methyl derivatives of adenosine, cytidine, guanosine, and uridine) are also contemplated.

Further, although described primarily in terms of DNA templates, such modified bases can be modified RNA bases and can be detected in RNA (or primarily RNA) templates. These and other modifications are known to those of ordinary skill in the art and are further described, e.g., in Narayan P, et al. (1987) Mol Cell Biol 7(4):1572-5; Horowitz S, et al. (1984) Proc Natl Acad Sci U.S.A. 81(18):5667-71; "RNA's Outfits: The nucleic acid has dozens of chemical costumes," (2009) C&EN; 87(36):65-68; Kriaucionis, et al. (2009) Science 324 (5929): 929-30; and Tahiliani, et al. (2009) Science 324 (5929): 930-35; Matray, et al. (1999) Nature 399(6737):704-8; Ooi, et al. (2008) Cell 133: 1145-8; Petersson, et al. (2005) J Am Chem Soc. 127(5):1424-30; Johnson, et al. (2004) 32(6):1937-41; Kimoto, et al. (2007) Nucleic Acids Res. 35(16):5360-9; Ahle, et al. (2005) Nucleic Acids Res 33(10):3176; Krueger, et al., Curr Opinions in Chem Biology 2007, 11(6):588); Krueger, et al. (2009) Chemistry & Biology 16(3):242; McCullough, et al. (1999) Annual Rev of Biochem 68:255; Liu, et al. (2003) Science 302(5646):868-71; Limbach, et al. (1994) Nucl. Acids Res. 22(12):2183-2196; Wyatt, et al. (1953) Biochem. J. 55:774-782; Josse, et al. (1962) J. Biol. Chem. 237:1968-1976; Lariviere, et al. (2004) J. Biol. Chem. 279:34715-34720; and in International Application Publication No. WO/2009/037473, the disclosures of which are incorporated herein by reference in their entireties for all purposes. Modifications further include the presence of non-natural (e.g., non-standard, synthetic, etc.) base pairs in the template nucleic acid, including but not limited to hydroxypyridone and pyridopurine homo- and hetero-base pairs, pyridine-2, 6-dicarboxylate and pyridine metallo-base pairs, pyridine-2,6-dicarboxamide and a pyridine metallo-base pairs, metal-mediated pyrimidine base pairs T-Hg(II)-T and C—Ag(I)-C, and metallo-homo-basepairs of 2,6-bis(ethylthiomethyl) pyridine nucleobases Spy, 6-amino-5-nitro-3-(1'-β-D-2'-deoxyribofuranosyl)-2(1H)-pyridone (dZ), 2-amino-8-(1'-β-D-2'-deoxyribofuranosyl)-imidazo[1,2-a]-1,3,5-triazin-4 (8H)-one (dP), and alkyne-, enamine-, alcohol-, imidazole-, guanidine-, and pyridyl-substitutions to the purine or pyridimine base (Wettig, et al. (2003) J Inorg Biochem 94:94-99; Clever, et al. (2005) Angew Chem Int Ed 117:7370-7374; Schlegel, et al. (2009) Org Biomol Chem 7(3):476-82; Zimmerman, et al. (2004) Bioorg Chem 32(1):13-25; Yanagida, et al. (2007) Nucleic Acids Symp Ser (Oxf) 51:179-80; Zimmerman (2002) J Am Chem Soc 124(46): 13684-5; Buncel, et al. (1985) Inorg Biochem 25:61-73; Ono, et al. (2004) Angew Chem 43:4300-4302; Lee, et al. (1993) Biochem Cell Biol 71:162-168; Loakes, et al. (2009), Chem Commun 4619-4631; Yang, et al. (2007) Nucleic Acids Res. 35(13):4238-4249; Yang, et al. (2006) Nucleic Acids Res. 34(21):6095-6101; Geyer, et al. (2003) Structure 11: 1485-1498; and Seo, et al. (2009) J Am Chem Soc 131:3246-3252, all incorporated herein by reference in their entireties for all purposes).

Other types of modifications include, e.g., a nick, a missing base (e.g., apurinic or apyridinic sites), a ribonucleoside (or modified ribonucleoside) within a deoxyribonucleoside-based nucleic acid, a deoxyribonucleoside (or modified deoxyribonucleoside) within a ribonucleoside-based nucleic acid, a pyrimidine dimer (e.g., thymine dimer or cyclobutane pyrimidine dimer), a cis-platin crosslinking, oxidation damage, hydrolysis damage, other methylated bases, bulky DNA or RNA base adducts, photochemistry reaction products, interstrand crosslinking products, mismatched bases, and other types of "damage" to the nucleic acid. As such, certain embodiments described herein refer to "damage" and such damage is also considered a modification of the nucleic acid in accordance with the present invention. Modified nucleotides can be caused by exposure of the DNA to radiation (e.g., UV), carcinogenic chemicals, crosslinking agents (e.g., formaldehyde), certain enzymes (e.g., nickases, glycosylases, exonucleases, methylases, other nucleases, glucosyltransferases, etc.), viruses, toxins and other chemicals, thermal disruptions, and the like. In vivo, DNA damage is a major source of mutations leading to various diseases including cancer, cardiovascular disease, and nervous system diseases (see, e.g., Lindahl, T. (1993) Nature 362(6422): 709-15, which is incorporated herein by reference in its entirety for all purposes). The methods and systems provided herein can also be used to detect various conformations of DNA, in particular, secondary structure forms such as hairpin loops, stem-loops, internal loops, bulges, pseudoknots, base-triples, supercoiling, internal hybridization, and the like; and are also useful for detection of agents interacting with the nucleic acid, e.g., bound proteins or other moieties.

In certain aspects, methods, compositions, and systems for detection and/or reversal of modifications in a template for single-molecule sequencing are provided, as well as determination of their location (i.e. "mapping") within a nucleic acid molecule. In certain preferred embodiments, the methods of the invention are used to detect the presence of such modified sites and to determine their location on the DNA template, e.g., by monitoring the progress and/or kinetics of a polymerase enzyme processing the template. For example, when a translating enzyme encounters certain types of damage or other modifications in a DNA template, the progress of the translating enzyme can be temporarily or permanently blocked, e.g., resulting in a paused or dissociated polymerase. As such, the detection of a pause in or termination is indicative of the presence of such damage or lesion.

The translating enzymes used in the invention can be modified in order to improve their performance. For example, various different polymerases may be used in template-directed sequence reactions, e.g., those described at length, e.g., in U.S. Pat. No. 7,476,503, the disclosure of which is incorporated herein by reference in its entirety for all purposes. In brief, the polymerase enzymes suitable for the present invention can be any nucleic acid polymerases that are capable of catalyzing template-directed polymerization with reasonable synthesis fidelity. The polymerases can be DNA polymerases or RNA polymerases (including, e.g., reverse transcriptases), DNA-dependent or RNA-dependent polymerases, thermostable polymerases or thermally degradable polymerases, and wild type or modified polymerases. In some embodiments, the polymerases exhibit enhanced efficiency as compared to the wild type enzymes for incorporating unconventional or modified nucleotides, e.g., nucleotides linked with fluorophores. In certain preferred embodiments, the methods are carried out with polymerases exhibiting a high degree of processivity, i.e., the ability to synthesize long stretches (e.g., over about 10 kilobases) of nucleic acid by maintaining a stable nucleic acid/enzyme complex. In certain preferred embodiments, sequencing is performed with polymerases capable of rolling circle replication. A preferred rolling circle polymerase exhibits strand-displacement activity, and as such, a single circular template can be sequenced repeatedly to produce a sequence read comprising multiple copies of the complement of the template strand by displacing the nascent strand ahead of the translocating polymerase. Since the methods of the invention can increase processivity of the polymerase by removing lesions that block continued polymerization, they are particularly useful for applications in which a long nascent strand is desired, e.g. as in the case of rolling-circle replication. Non-limiting examples of rolling circle polymerases suitable for the present invention include but are not limited to T5 DNA polymerase, T4 DNA polymerase holoenzyme, phage M2 DNA polymerase, phage PRD1 DNA polymerase, Klenow fragment of DNA polymerase, and certain polymerases that are modified or unmodified and chosen or derived from the phages Φ129 (Phi29), PRD1, Cp-1, Cp-5, Cp-7, Φ15, Φ1, Φ21, Φ25, BS 32 L17, PZE, PZA, Nf, M2Y (or M2), PR4, PR5, PR722, B103, SF5, GA-1, and related members of the Podoviridae family. In certain preferred embodiments, the polymerase is a modified Phi29 DNA polymerase, e.g., as described in U.S. Patent Publication No. 20080108082, incorporated herein by reference in its entirety for all purposes. Additional polymerases are provided, e.g., in U.S. Ser. No. 11/645,125, filed Dec. 21, 2006; Ser. No. 11/645,135, filed Dec. 21, 2006; Ser. No. 12/384,112, filed Mar. 30, 2009; and 61/094,843, filed Sep. 5, 2008; as well as in U.S. Patent Publication No. 20070196846, the disclosures of which are incorporated herein by reference in their entireties for all purposes.

Certain embodiments use non-natural base pairs that are orthogonal to the natural nucleobases pairs. For example, isoguanine (isoG) can be incorporated by a polymerase into DNA at sites complementary to isocytosine (isoC) or 5-methylisocytosine ($^{Me}$isoC), and vice versa, as shown by the following chemical structure and described in A. T. Krueger, et al., "Redesigning the Architecture of the Base Pair: Toward Biochemical and Biological Function of New Genetic Sets." *Chemistry & Biology* 2009, 16(3), 242, incorporated herein by reference in its entirety for all purposes.

Other non-natural base pairs that are orthogonal to the natural nucleobases pairs can also be used, e.g., Im-N$^O$/Im-O$^N$, dP/dZ, or A*/T* (described further in Yang, et al. (2007) Nucleic Acids Res. 35(13):4238-4249; Yang, et al. (2006) Nucleic Acids Res. 34(21):6095-6101; Geyer, et al. (2003) Structure 11: 1485-1498; J. D. Ahle, et al., *Nucleic Acids Res* 2005, 33(10), 3176; A. T. Krueger, et al., supra; and A. T. Krueger, et al., Curr Opinions in Chem Biology 2007, 11(6), 588).

In certain embodiments, a nucleic acid modification to be detected by the methods herein is 7,8-dihydro-8-oxoguanine ("8-oxoG") (also known as 8-oxo-7,8-dihydroguanine, 8-oxoguanine, and 8-hydroxyguanine). 8-oxoG is the major oxidative DNA lesion found in human tissue. Due to the relatively subtle modification to guanine in 8-oxoG, it may be bypassed by replicative DNA polymerases, which preferentially incorporate an adenine nucleotide into the nascent nucleic acid strand at the position where the complementary cytosine should be incorporated, thereby resulting in a mutation in the nascent strand (see, e.g., Hsu, et al. (2004) Nature 431(7005): 217-21; and Hanes, et al. (2006) J. Biol. Chem. 281:36241-8, which are incorporated herein by reference in their entireties for all purposes). As well as introducing mutations in vivo, the bypass of such lesions by a polymerase during template-dependent sequencing reactions introduces errors into the sequence reads generated, and the presence of the damaged guanine nucleotide can also cause base misalignment, potentially adding further errors into a resulting sequence read. DNA synthesis opposite an 8-oxoG lesion has relatively very low specificity (kcat/Km) that is about 10$^6$-fold lower than incorporating a C opposite an unmodified G. See, e.g., Hsu, et al., supra. Further, due to its very low redox potential 8-oxoG can be more easily oxidized than unmodified guanine, and the 8-oxoG oxidation products are very effective blockers of DNA polymerases. See, e.g., Duarte, et al. (1999) Nucleic Acids Res 27(2):496-502; and Kornyushyna, et al. (2002) Biochemistry 41(51): 15304-14, the disclosures of which are incorporated herein by reference in their entireties for all purposes.

It has been shown that 8-oxoG alters both $k_{cat}$ and $K_m$ of steady-state incorporation kinetics, which are likely to cause an altered ITD before incorporation of a nucleotide (G or A) into the complementary position in the nascent strand during template-directed sequencing reactions (see, e.g., Hsu, et al. and Hanes, et al., supra). These altered kinetic characteristics can be used to detect 8-oxoG in a template nucleic acid during real-time sequencing reactions. Further, a circular template that comprises both complementary strands of a region of interest (e.g., as described in U.S. Ser. Nos. 12/383,855 and 12/413,258, both filed Mar. 27, 2009 and incorporated herein by reference in their entireties for all purposes) can be used to repeatedly sequence both strands of a region of interest, thereby generating redundant sequence information that can be analyzed to statistically determine how often a given position in the template has an A-G mismatch as compared to how often the correct base is incorporated at that position. The redundant sequence information increases the accuracy of correctly calling a position as a G or an 8-oxoG. For example, if the mismatch rate is 100%, then if one detects an A at the position, but then a G at the complementary position, then it is highly likely that the A detected was Hoogsteen base pairing with an 8-oxoG in the template. This strategy is similar to detection of 5-MeC modifications that have been deaminated to uracil prior to sequencing, as described in greater detail below.

The mismatch incorporation rate opposite 8-oxoG sites, as well as the degree to which ITD is affected by 8-oxoG depend on the type of polymerase used in the reaction (see, e.g., Hsu, et al. and Hanes, et al., supra). As such, polymerase mutants can be designed to have increased kinetic sensitivity to 8-oxoG, or increased/decreased misincorporation rate opposite an 8-oxoG. Methods for designing polymerases for various embodiments of the invention are known in the art and provided elsewhere herein. Further, multiple binding events are very likely at the site of modification, resulting in one or more signals not associated with incorporation into the nascent strand, and these multiple binding events can also occur at positions proximal to the modification, e.g., continuing for a few bases after the site of damage. These additional signaling events would provide a robust indicator of the site of modification. In addition, multiple sequencing reads for the region of the template comprising the modification are expected to contain variable numbers of extra signaling events at or proximal to the modification. As such, comparison of this redundant sequence data will also facilitate identification of loci comprising the modification.

In some aspects, base J is detected and/or mapped in a sample nucleic acid. Base J is a DNA modification found in certain species of trypanosomes, including the one responsible for African sleeping sickness, which afflicts hundreds of thousands of people per year. It is the result of two enzymatic steps. First, thymidine-hydroxylase converts dT into hydroxymethyluracil (HOMedU); second, β-glucosyl-transferase converts HOMedU into base J (β-D-glucosyl-HOMedU or "dJ"). Base J is found predominantly in telomeric repeat genomic regions and is involved in expression of variant surface glycoproteins (VSG), which are important for mammalian host infection. The present invention provides methods for precise mapping of genomic locations of base J that do not require the conventional detection methods of thin layer chromatography, mass spectrometry, or base J-specific antibodies. The single-molecule sequencing-by-incorporation methods described herein facilitate real-time detection of base J in a template during polymerase-mediated nascent strand synthesis. The impact of base J on polymerase activity allow detection of the base in a template nucleic acid, and the sequence data generated during the reaction provides the nucleotide sequence of the region comprising the modified base. Further, sequencing kinetics can also distinguish between HOMedU and base J in a template, thus providing information about the efficiency and rate of enzymatic conversion from one modified base to the other. As such, such sequencing operations can be used to map precise locations of base J and HOMedU in the trypanosome genome, and this information will help elucidate its role in disease. For more information on base J, see Borst, et al. (2008) Annu. Rev. Microbiol. 62:235-51, incorporated by reference herein in its entirety for all purposes.

Direct detection of modifications (e.g., methylated bases as described above) without pre-treatment of the DNA sample, has many benefits. Alternatively or additionally, complementary techniques may be employed, such as the use of non-natural or modified nucleotide analogs and/or base pairing described elsewhere herein. In general, such complementary techniques serve to enhance the detection of the modification, e.g., by amplifying a signal indicative of the modification. Further, while the methods described herein focus primarily on detection of 5-MeC nucleotides, it will be clear to those of ordinary skill in the art that these methods can also be extended to detection of other types of nucleotide modifications or damage. In addition, since certain sequencing technologies (e.g., SMRT™ sequencing) do not require amplification of the template, e.g., by PCR, other chemical modifications of the 5-MeC or other modifications can be employed to facilitate detection of these modified nucleotides in the template, e.g., by employing modifying agents that introduce additional modifications into the template at or proximal to the modified nucleotides. For example, the difference in redox potential between normal cytosine and 5-MeC can be used to selectively oxidize 5-MeC and further distinguish it from the nonmethylated base. Such methods are further described elsewhere, and include halogen modification (S. Bareyt, et al., Angew Chem Int Ed Engl 2008, 47(1), 181) and selective osmium oxidation (A. Okamoto, Nucleosides Nucleotides Nucleic Acids 2007, 26(10-12), 1601; and K. Tanaka, et al., J Am Chem Soc 2007, 129(17), 5612), and these references are incorporated herein by reference in their entireties for all purposes.

By way of example, DNA glycosylases are a family of repair enzymes that excise altered (e.g., methylated), damaged, or mismatched nucleotide residues in DNA while leaving the sugar-phosphate backbone intact. Additional information on glycosylase mechanisms and structures is provided in the art, e.g., in A. K. McCullough, et al., *Annual Rev of Biochem* 1999, 68, 255. In particular, four DNA glycosylases (ROS1, DME, DML2, and DML3) have been identified in *Arabidopsis thaliana* that remove methylated cytosine from double-stranded DNA, leaving an abasic site. (See, e.g., S. K. Ooi, et al., *Cell* 2008, 133, 1145, incorporated herein by reference in its entirety for all purposes.) Furthermore, it has been shown that a 5'-triphosphate derivative of the pyrene nucleoside (dPTP) is efficiently and specifically inserted by certain DNA polymerases into abasic DNA sites through steric complementarity. (See, e.g., T. J. Matray, et al., *Nature* 1999, 399(6737), 704, incorporated herein by reference in its entirety for all purposes.)

In certain embodiments of single-molecule, five-color DNA methylation sequencing, DNA glycosylase activity can be combined with polymerase incorporation of a non-natural nucleotide analog (e.g., a pyrene analog (dPTP) as shown in FIG. 4). For example, in certain embodiments, methylated cytosines are excised from a DNA sample treated with an *Arabidopsis* DNA glycosylase. Covalent linkage of a fifth fluorophore to the terminal phosphate of dPTP allows detection of abasic sites during polymerase-mediated DNA synthesis.

In certain embodiments, the template may be modified by treatment with bisulfite. Bisulfite sequencing is a common method for analyzing CpG methylation patterns in DNA. Bisulfite treatment deaminates unmethylated cytosine in a single-stranded nucleic acid to form uracil (P. W. Laird, Nat Rev Cancer 2003, 3(4), 253; and H. Hayatsu, *Mutation Research* 2008, 659, 77, incorporated herein by reference in their entireties for all purposes). In contrast, the modified 5-MeC base is resistant to treatment with bisulfite. As such, pretreatment of template DNA with bisulfite will convert cytosines to uracils, and subsequent sequencing reads will contain guanine incorporations opposite 5-MeC nucleotides in the template and adenine incorporations opposite the uracil (previously unmethylated cytosine) nucleotides. If a nucleic acid to be treated with bisulfite is double-stranded, it is denatured prior to treatment. In conventional methods, amplification, e.g., PCR, typically precedes sequencing, which amplifies the modified nucleic acid, but does not preserve information about the complementary strand. In contrast, certain embodiments of the present invention include use of a template molecule comprising both strands of a double-stranded nucleic acid that can be converted to a single-stranded molecule, e.g., by adjusting pH, temperature, etc. Treatment of the single-stranded molecule with bisulfite is followed by single-molecule sequencing, and because the template retains both strands of the original nucleic acid, sequence information from both is generated. Comparison of the resulting sequence reads for each strand of the double-stranded nucleic acid will identify positions at which an unmethylated cytosine was converted to uracil in the original templates since the reads from the two templates will be non-complementary at that position (A-C mismatch). Likewise, reads from the two templates will be complementary at a cytosine position (G-C match) where the cytosine position was methylated in the original template. In certain preferred embodiments, a circular template is used, preferably having regions of internal complementarity that can hybridize to form a double-stranded region, e.g., as described in U.S. Ser. No. 12/383,855 and U.S. Ser. No. 12/413,258, both filed on Mar. 27, 2009, and both incorporated herein by reference in their entireties for all purposes.

Methylcytosine can have an effect on ITD over a number of neighboring positions when compared to non-methylated cytosine. Uracil compared to thymine is like unmethylated cytosine compared to methylcytosine (i.e. the only difference between U and T is that T has an additional methyl group). Thus, the invention provides methods for performing bisulfite sequencing in which the polymerase kinetics or the mismatch incorporation rate are monitored in addition to the actual nucleotides being incorporated. Detection of a change in either of these kinetic parameters or in the mismatch rate at the position in question, or at neighboring positions, is used to determine whether or not a position was always a T or is a U that was originally an unmethylated cytosine.

In yet further embodiments, a template nucleic acid is exposed to a reagent that transforms a modified nucleotide to a different nucleotide structure. For example, a bacterial cytosine methyl transferase converts 5-MeC to thymine (M. J. Yebra, et al., Biochemistry 1995, 34(45), 14752, incorporated herein by reference in its entirety for all purposes). Alternatively, the reagent may convert a methyl-cytosine to 5-hydroxy-methylcytosine, e.g., the hydroxylase enzyme TET1 (M. Tahiliani, et al., Science 2009, 324(5929), 930, incorporated herein by reference in its entirety for all purposes). In further embodiments, the reagent may include a cytidine deaminase that converts methyl-cytosine to thymine (H. D. Morgan, et al., J Biological Chem 2004, 279, 52353, incorporated herein by reference in its entirety for all purposes). In yet further embodiments, a restriction enzyme that specifically alters a modification of interest can be used to create a lesion at the modification site. For example, DPNI cleaves at a recognition site comprising methyladenosine. Optionally, the cleaved template could be repaired during an analytical reaction by inclusion of a ligase enzyme in the reaction mixture. As noted elsewhere herein, nucleotides other than 5-MeC can also be modified and detected by the methods provided herein. For example, adenine can be converted to inosine through deamination, and this conversion affected by methylation of adenine, allowing differential treatment and detection of adenine.

In certain embodiments, modification of the template by addition of bulky group to 5-hmC facilitates detection of 5-hmC and its discrimination from 5-MeC and unmodified cytosine. In particular, certain electrophilic compounds have been shown to react specifically with hydroxyl groups of nucleic acids under mild conditions in aqueous solution, resulting in addition of a bulky adduct to the nucleic acids. For example, selective acylation of the ribose 2'-hydroxyl position using N-methylisatoic anhydride (NMIA) and selective 2'-hydroxyl acylation analyzed by primer extension (SHAPE) to analyze local tRNAAsp transcript structure in yeast tRNAAsp have been demonstrated. (See, e.g., Merino, et al. (2005) J. Am. Chem. Soc. 127: 4223-4231, which is incorporated herein by reference in its entirety for all purposes.) Additionally, procedures for selective modification of RNA with the spin label N-(2,2',5,5') tetramethyl-3-carboxypyrrolidine-1-oxyl)-imidazole have been developed. This spin label was shown to interact with hydroxyl groups of 5-hydroxymethyl-2 deoxycytidines and the 2' OH ribose groups of polynucleotides and to transfer a bulky adduct to the bases. The modification did not affect secondary structure, conformation, or template properties in a cell-free system. (See, e.g., Petrov, A. I. (1980) Nuc. Ac. Res. 8(23):5913-5929; Petrov, et al. (1980) Nuc. Ac. Res. 8(18):4221-4234; and Kamzolova, S. G. (1987) Biokhimiia 52(9):1577-82, the disclosures of which are incorporated herein by reference in their entireties for all purposes.) In addition, carbonyldiimidazone (CDI) also reacts with hydroxymethyl groups to transfer a bulky adduct. FIG. 5 provides a schematic showing addition of bulky base adducts to 5-hmC by treatment with NMIA (A) and CDI (B). One potential outcome of the instant methods is the additional modification of terminal phosphate or other hydroxyl groups of a nucleoside. Addition of a bulky group at the OH group of 5-hmC alters the kinetics of the DNA polymerase-mediated incorporation of a nucleoside into a nascent strand opposite the modified 5-hmC, and this alteration facilitates detection and mapping of the 5-hmC within a template nucleic acid. These and other electrophilic compounds known in the art can be used similarly to those described above to add bulky adducts to nucleic acids and, thereby, provide a characteristic kinetic signature during single molecule sequencing reactions that is indicative of the presence of a given base so modified.

In certain embodiments, DNA glucosyltransferases are used to transfer a glucose group to 5-hmC. DNA glucosyltransferases found in bacteriophage-infected *E. coli* transfer glucose from uridine diphosphate glucose (UDP-glucose) to hmC nucleotides in DNA. These enzymes are similar to the glucosyltransferase in trypanosomes that converts hydroxymethyluracil to base J, as described above.

Exemplary enzymes for transferring glucose groups to hmC include, but are not limited to, T2-hmC-α-glucosyltransferase, T4-hmC-α-glucosyltransferase, T6-hmC-α-glucosyltransferase, and T2-hmC-β-glucosyltransferase. Other enzymes can be used to create diglucosylated hmC, such as T6-glucosyl-hmC-β-glucosyltransferase, which creates diglucosylated hmC with a β3 linkage between the two glucose groups. These enzymes are generally specific for hmC and do not typically alter other bases such as A, C, MeC, T, or G. As such, treating hmC-containing nucleic acids with such enzymes creates nucleic acids in which the hmC residues have been converted to monoglucosylated-hmC or multi-glucosylated-hmC. Glucosylated-hmC is much larger and bulkier than hmC, and therefore has a distinctive effect on polymerase activity when present in a template nucleic acid. Details on the glucosylation of 5-hmC by glucosyltransferases are known in the art, e.g., in Josse, et al. (1962) J. Biol. Chem. 237:1968-1976; and Lariviere, et al. (2004) J. Biol. Chem. 279:34715-34720.

In certain embodiments, the template may be modified by treatment with dimethyl sulfate (DMS) prior to sequencing. DMS is a chemical that methylates the N7 position of guanine in dsDNA, and to a lesser extent the N3 position of adenine in dsDNA. If proteins are bound to a DNA treated with DMS, the proteins will block the methylation of the sequences to which they are bound. The bound proteins can then be removed and the DNA treated with piperidine, which breaks the DNA backbone by removal of the methylated bases. Protected regions of the DNA are identified as having been bound to the proteins during the DMS treatment. DMS also modifies the N3 position of cytosine and the N1 position of adenine in single-stranded DNA or RNA so these bases can no longer base pair with their complement. Since both these positions are involved in base-pairing, regions that are double-stranded during DMS treatment are protected from modification. Reverse transcriptase PCR and gel analysis is subsequently used to identify regions that were unmodified, and are therefore likely regions that adopt secondary structures that protect them from DMS treatment.

Detection of Agent-Nucleic Acid Interactions

Another example of a biological process that may be monitored in accordance with the invention is association of a nucleic acid binding agent (e.g., a protein, nucleic acid, or small molecule) with a single nucleic acid molecule. As for the chemical modifications to the template described above, use of such agents can serve to enhance the detection of the modification, e.g., by amplifying a signal indicative of the modification. Further, the methods are useful for mapping binding sites of binding agents that bind to a natural or unmodified nucleotide in a nucleic acid molecule. Many types of agents bind to nucleic acids, such as transcription factors, RNA and DNA polymerases, reverse transcriptases, histones, nucleases, restriction enzymes, replication protein A (RPA), single-stranded binding protein (SSB), RNA-binding proteins, microRNA-containing ribonucleoprotein complexes, anti-DNA antibodies, DNA damage-binding agents, modifying agents, agents that bind altered nucleotides (e.g., methylated), small RNAs, microRNAs, drug targets, etc. In particular, transcription factors are involved in gene expression regulation and are thus very important for the study of diseases such as cancer. Further, RPA binds single-stranded DNA during replication to keep DNA unwound and accessible to the polymerase. Current technologies for detecting the binding of a protein transcription factor to a DNA molecule involve bulk detection. Certain aspects of the invention provide methods for detecting the binding of a transcription factor or other nucleic acid binding agent to a single molecule of DNA. In some embodiments, the binding agents are detected while bound to a nucleic acid template; in some embodiments the positions at which the binding agents were associated are detected after the binding agents have dissociated or been removed from the template. The advantages of the methods described herein include, but are not limited to, improved resolution of kinetics (e.g., of association and dissociation), binding loci, and statistical analysis; and greater sensitivity and simplicity.

Data Analysis

Analysis of the data generated by the methods described herein is generally performed using software and/or statistical algorithms that perform various data conversions, e.g., conversion of signal emissions into basecalls, conversion of basecalls into consensus sequences for a nucleic acid template, and conversion of various aspects of the basecalls and/or consensus sequence to derive a reliability metric for the resulting values. Such software, statistical algorithms, and use thereof are described in detail, e.g., in U.S. Patent Publication No. 20090024331 and U.S. Ser. No. 61/116,439, the disclosures of which are incorporated herein by reference in their entireties for all purposes. Specific methods for discerning altered nucleotides in a template nucleic acid are provided in U.S. Ser. No. 61/201,551, filed Dec. 11, 2008, and incorporated herein by reference in its entirety for all purposes. These methods include use of statistical classification algorithms that analyze the signal from a single-molecule sequencing technology and detect significant changes in one or more aspects of signal morphology, variation of reaction conditions, and adjustment of data collection parameters to increase sensitivity to changes in signal due to the presence of modified or damaged nucleotides.

In certain aspects, the invention provides methods for detecting changes in the kinetics (e.g., slowing or pausing, changes in inter transition duration, or changes in the kinetics of cognate or non-cognate sampling) or other reaction data for real-time DNA sequencing. As discussed at length above, detection of a change in such sequencing applications can be indicative of secondary structure in the template, the presence of modifications in the template, the presence of an agent bound to the template, and the like. It is appreciated that the kinetic activity of single molecules does not follow the regular and simple picture implied by traditional chemical kinetics, a view dominated by single-rate exponentials and the smooth results of ensemble averaging. In a large multi-dimensional molecular system, such as the polymerase-DNA complex, there are processes taking place on many different time scales, and the resultant kinetic picture can be quite complex at the molecular level. (See, e.g., Herbert, et al. (2008) Ann Rev Biochem 77:149.) As such, a real-time single-molecule sequencing technology should be adaptable to such non-exponential behavior. For example, pauses during a real-time sequencing reaction are detectable as regions in the trace of observed signals over time in which it appears that the enzyme has significantly slowed as compared to the average rate of incorporation. As such, methods are provided to analyze the data generated in the vicinity of a pause site, and in particular algorithmic methods for classifying and removing or down-weighting the occurrence of pauses in the context of single-molecule sequencing. General information on algorithms for use in sequence analysis can be found, e.g., in Braun, et al. (1998) Statist Sci 13:142; and Durbin, et al. (1998) *Biological sequence analysis: Probabilistic models of proteins and nucleic acids*, Cambridge University Press: Cambridge, UK.

Systems

The invention also provides systems that are used in conjunction with the compositions and methods of the invention in order to provide for real-time single-molecule detection of analytical reactions. The nanopores are generally provides as arrays of nanopores having 100s to millions of nanopores. See e.g. US 20100331194, and U.S. Ser. No. 13/083,320 filed Apr. 8, 2011. Such arrays are connected to electrical systems which provide the drive voltage across the pores and measure the electrical characteristics of the pore including transport current through the pore, capacitance, and electron tunneling current. In particular, such systems typically include the reagent systems described herein, in conjunction with an analytical system, e.g., for detecting data from those reagent systems. The systems of the invention also typically include information processors or computers operably coupled to the detection portions of the systems, in order to store the signal data obtained from the detector(s) on a computer readable medium, e.g., hard disk, CD, DVD or other optical medium, flash memory device, or the like. For purposes of this aspect of the invention, such operable connection provides for the electronic transfer of data from the detection system to the processor for subsequent analysis and conversion. Operable connections may be accomplished through any of a variety of well-known computer networking or connecting methods, e.g., Firewire®, USB connections, wireless connections, WAN or LAN connections, or other connections that preferably include high data transfer rates. The computers also typically include software that analyzes the raw signal data, identifies signals that are likely associated with incorporation events, and identifies bases incorporated during the sequencing reaction, in order to convert or transform the raw signal data into user interpretable sequence data.

Further, the invention provides data processing systems for transforming raw data generated in an analytical reaction into analytical data that provides a measure of one or more aspects of the reaction under investigation, e.g., transforming signals from a sequencing-by-synthesis reaction into nucleic acid sequence read data, which can then be transformed into consensus sequence data. In certain embodiments, the data processing systems include machines for generating nucleic acid sequence read data by polymerase-mediated processing of a template nucleic acid molecule (e.g., DNA or RNA). The nucleic acid sequence read data generated is representative of the nucleic acid sequence of the nascent polynucleotide synthesized by a polymerase translocating along a nucleic acid template only to the extent that a given sequencing technology is able to generate such data, and so may not be identical to the actual sequence of the nascent polynucleotide molecule. For example, it may contain a deletion or a different nucleotide at a given position as compared to the actual sequence of the polynucleotide, e.g., when a nucleotide incorporation is missed or incorrectly determined, respectively. As such, it is beneficial to generate redundant nucleic acid sequence read data, and to transform the redundant nucleic acid sequence read data into consensus nucleic acid sequence data that is generally more representative of the actual sequence of the polynucleotide molecule than nucleic acid sequence read data from a single read of the nucleic acid molecule. Redundant nucleic acid sequence read data comprises multiple reads, each of which includes at least a portion of nucleic acid sequence read that overlaps with at least a portion of at least one other of the multiple nucleic acid sequence reads. As such, the multiple reads need not all overlap with one another, and a first subset may overlap for a different portion of the nucleic acid sequence than does a second subset. Such redundant sequence read data can be generated by various methods, including repeated synthesis of nascent polynucleotides from a single nucleic acid template, synthesis of polynucleotides from multiple identical nucleic acid templates, or a combination thereof.

In another aspect, the data processing systems can include software and algorithm implementations provided herein, e.g. those configured to transform redundant nucleic acid sequence read data into consensus nucleic acid sequence data, which, as noted above, is generally more representative of the actual sequence of the nascent polynucleotide molecule than nucleic acid sequence read data from a single read of a single nucleic acid molecule. Further, the transformation of the redundant nucleic acid sequence read data into consensus nucleic acid sequence data identifies and negates some or all of the single-read variation between the multiple reads in the redundant nucleic acid sequence read data. As such, the transformation provides a representation of the actual nucleic acid sequence of the nascent polynucleotide complementary to the nucleic acid template that is more accurate than a representation based on a single read.

Various methods and algorithms for data transformation employ data analysis techniques that are familiar in a number of technical fields, and are generally referred to herein as statistical analysis.

The software and algorithm implementations provided herein are preferably machine-implemented methods, e.g., carried out on a machine comprising computer-readable medium configured to carry out various aspects of the methods herein. For example, the computer-readable medium preferably comprises at least one or more of the following: a) a user interface; b) memory for storing raw analytical reaction data; c) memory storing software-implemented instructions for carrying out the algorithms for transforming the raw analytical reaction data into transformed data that characterizes one or more aspects of the reaction (e.g., rate, consensus sequence data, etc.); d) a processor for executing the instructions; e) software for recording the results of the transformation into memory; and f) memory for recordation and storage of the transformed data. In preferred embodiments, the user interface is used by the practitioner to manage various aspects of the machine, e.g., to direct the machine to carry out the various steps in the transformation of raw data into transformed data, recordation of the results of the transformation, and management of the transformed data stored in memory.

As such, in preferred embodiments, the methods further comprise a transformation of the computer-readable medium by recordation of the raw analytical reaction data and/or the transformed data generated by the methods. Further, the computer-readable medium may comprise software for providing a graphical representation of the raw analytical reaction data and/or the transformed data, and the graphical representation may be provided, e.g., in soft-copy (e.g., on an electronic display) and/or hard-copy (e.g., on a print-out) form.

The invention also provides a computer program product comprising a computer-readable medium having a computer-readable program code embodied therein, the computer readable program code adapted to implement one or more of the methods described herein, and optionally also providing storage for the results of the methods of the invention. In certain preferred embodiments, the computer program product comprises the computer-readable medium described above.

In another aspect, the invention provides data processing systems for transforming raw analytical reaction data from one or more analytical reactions into transformed data representative of a particular characteristic of an analytical reaction, e.g., an actual sequence of one or more template nucleic acids analyzed, a rate of an enzyme-mediated reaction, an identity of a kinase target molecule, and the like. Such data processing systems typically comprise a computer processor for processing the raw data according to the steps and methods described herein, and computer usable medium for storage of the raw data and/or the results of one or more steps of the transformation, such as the computer-readable medium described above.

Error Control by Measuring the Same Sequence in Two Different Nanopore Types

In some aspects, the invention provides for improving error rates in nanopore sequencing by measuring the same nucleotide sequence in two different types of pores and combining the information from both measurements to obtain a lower overall error rate. In some aspects the invention provides for improved error rates by measuring the same nucleotide sequence under different conditions and using the different error rates under each of the conditions to lower the overall error rate. In some cases, the sequence of the same molecule is measured. In some cases, the same sequence is measured on different molecules and compared.

In some cases sequencing of a single molecule in a pore is carried out multiple times as described herein, and the conditions of the reaction are altered such that a different error profile will be obtained. Methods of the invention include providing first and second reaction condition; carrying out nanopore sequencing under the first and second reaction condition, either simultaneously or sequentially; obtaining first and second sets of sequencing data from the analytical reaction under the first and second sequencing conditions, respectively; and analyzing the first set of sequencing data and the set of second sequencing data in combination to determine a final set of sequencing data that is more reflective of the sequence of the template nucleic acid than either the first set of sequencing data or the set of second sequencing data alone.

The first and second sequencing conditions can be provided at a single reaction region, or a different reaction regions, e.g., in an array. In certain embodiments, the first sequencing condition comprises a first nanopore and the second sequencing condition comprises a second nanopore, and the first and second nanopores have different characteristics during the analytical reaction. For example, the first nanopore and second nanopore can have different error profiles, e.g., complementary error profiles. The first and second nanopore can optionally be localized in different reaction regions. In yet further embodiments, the first sequencing condition and the second sequencing conditions differ in at least one of the group consisting of temperature, pH, divalent cation concentration, buffer, and labeling groups present. In certain embodiments, at least one of the sequencing reactions is carried out iteratively to generate redundant reaction data in a single nanopore. In specific embodiments, the final set of reaction data comprises a consensus nucleotide sequence.

For example, the same molecule or multiple molecules having substantially the same sequence are sequenced in both pore 1 and pore 2. The error profiles for each of pore 1 and pore 2 are different, that is each profile has a different reputation, for example with pore 1 more accurate in some sequence contexts, and pore 2 more accurate in other sequence contexts. The sequencing data from each of these pores is combined to obtain higher accuracy than would be obtained by either pore 1 or pore 2 alone. Where the error tendency of each of the two pores is known and factored into the process, the process can be called reputation-based discrepancy adjudication. In some cases, a sample having a subset of molecules with the same sequence is run through an array of pores, and different types of pores in the array have different error profiles. In some cases, it is known which molecule is passing through which type of pore. In other cases, it is not known at the start which type of pore is at which location on the array, but it is known that there are multiple types, e.g. 2 types of pores.

Even where the type of pore is not known, in some cases, the type of pore that carried out the sequencing can be determined by the characteristics of the data obtained from that pore. This approach can be referred to accent-based attribution. The unique signal characteristics of a given type of pore can be thought of as an accent. The evaluation of the data from that type of pore includes its accent, which can be used to identify which type of pore it was. Once the type of pore is known, then the calling of the base can be influenced by applying the error characteristics of that type of pore. For example, where that type of pore is more accurate than another type of pore in a specific sequence context, the base calling can be done giving higher weight to the data from that type of pore for that type of sequence context. Alternatively, where a given type of pore is known to be more prone to a certain type of error, e.g. miscalls, then the base calling and/or alignment algorithm can take into account the propensity for that error in order to improve the overall accuracy of the sequencing.

Often the results of nanopore sequencing studies are influenced by various characteristics of the reaction conditions under which the studies are performed. Such reaction condition characteristics include temperature, pH, buffer, divalent cation composition, temperature, pH, and the particular reaction components that are interacting within the reaction, e.g., reactive proteins, enzyme, cofactors, substrates, binding agents/partners, etc. For example, the presence of a particular type of a given class of enzyme, substrate, cofactor, etc. as opposed to a different type of enzyme, substrate, cofactor, etc. is considered to be a characteristic of a reaction condition, and changing such a characteristic is considered changing the reaction condition. Changing the reaction conditions for a sequencing reaction can influence the reaction data, both directly and indirectly, e.g., by affecting the attributes and/or activities of the reaction components involved in the sequencing reaction. The differing impacts of various characteristics of reaction conditions on an sequencing reaction have traditionally confounded analysis of the reaction, e.g., by introducing bias, errors, and other inconsistencies that were difficult to identify during reaction data analysis. In certain aspects, the present invention instead takes advantage of these previously confounding reaction condition-based effects to provide higher quality reaction data by performing a nanopore sequencing reaction under different conditions, and using the data from these reactions together to analyze the analytical reaction. As such, the invention provides experimental systems in which an sequencing reaction performed under a first reaction condition provides a first data set, and the sequencing reaction performed under a second reaction condition provides a second data set. The first and second data sets are used together to determine a final data set that best represents the sequence of the template nucleic acid. In particular embodiments, inconsistencies between the first data set and the second data set are resolved by determining which sequencing reaction condition (e.g., the first reaction condition) provides the best environment for accurate data at that point in the sequencing reaction. For example, it may be determined that data from the first data set is more reliable at a first time point, and data from the second data set is more reliable at a second time point. Therefore, the data from the first data set (and not the second data set) is selected for inclusion in the final data set for the first time point, and the data from the second data set (and not the first data set) is selected for inclusion in the final data set for the second time point. The final data set thus comprises a combination of data from both the first and second data sets. In this way, condition-based bias in an experimental system can be selectively "cancelled out" by using different reaction conditions having different condition-based biases and the quality of the final data set is improved.

A sequencing reaction can be repeated on a single nanopore. Alternatively or in addition, a sequencing reaction can be repeated by simultaneously or sequentially performing it on multiple, different molecules or molecular complexes under the same or different reaction conditions. For example, multiple different types of nanopores can be used, e.g., by using two or more nanopores in series or stages and used to sequence the same template once or multiple times as described herein, thereby providing multiple different sequencing reaction conditions at multiple different nanopores. Methods and devices for performing nanopore sequencing with pores in series are described, for example, in US 2010/0331194 which is incorporated herein by reference for all purposes.

In some cases the sequence of a single template molecule is measured multiple times using a plurality of nanopores by exchanging the nanopore that is proximal to a bound template. For example, a template molecule can be attached to the surface proximate to the pore. The length of the template is selected such that the distance the template molecule is from the nanopore is short relative to the length of the template. For example, a template is attached at one end, and the remainder of the linear molecule will be moving around the surface such that the free end of the bound template can access the nanopore, and a portion of the template can be translated into the nanopore. As the template is translated into the nanopore, it can be sequenced as described herein. The driving voltage can be turned off or reversed in order for the template to translate back out of the nanopore. In some cases, sequence information can also be obtained as the template is reversed back out of the nanopore. Subsequently, the driving voltage can be used to drive the template into the pore again for another round of sequencing. Typically relatively long templates are used for this method, typically greater than 10,000 bases in length. The bound template can be for example, greater than about 50,000 bases in length, greater than 100,000 bases in length, greater than 300,000 bases in length, or greater than 600,000 bases in length. The template is bound from about 20 nm to about 10 microns from the nanopore, or from 100 nanometers to about 1 micron. Having the template nucleic acid nearer the nanopore allows for a greater portion of the template to be sequenced.

In some cases the characteristics of the pore can be changed between sequencing runs, allowing for obtaining sequence reads with different error profiles as described herein. The data from the sequencing runs can be combined to improve the accuracy of the sequencing over what could be obtained with a single type of nanopore.

In some cases, the nanopore is a solid state nanopore. In some cases, the nanopore is in a lipid layer. In other cases, the nanopore is a hybrid nanopore as described in more detail in US 2010/0331194, which is incorporated herein by reference for all purposes. Where the nanopore is a hybrid nanopore having a hole in a solid substrate the is filled with a region of lipid bilayer including a nanopore, the template molecule can be attached to the solid substrate proximate to the hole in the solid substrate. The scale of the hole including the lipid region is selected such that the free end of the bound template can diffuse into the nanopore in the lipid bilayer. This type of arrangement allows for repeated sequencing of the template nucleic acid in the nanopore, followed by exchange of the nanopore for another type of nanopore that has different sequencing error characteristics. For example, the template can be attached covalently or with a strong binding reagent such that it will remain attached to the substrate during the relatively mild conditions required to exchange the nanopore in the lipid bilayer region.

In further embodiments, multiple different types of nanopores are used with a template preparation that comprises a plurality of fragments of a nucleic acid sample of interest, e.g., an amplified nucleic acid sample. For example, a genomic DNA or RNA sample can be amplified, e.g., by whole genome amplification or random amplification methods, and the resulting amplicons sequenced in a reaction mixture comprising a plurality nanopores, where the plurality optionally comprises different types of nanopores. In such embodiments, the template preparation does not necessarily comprise identical template molecules, especially when fragmentation or amplification is randomized. However, a particular nucleotide sequence or region of interest is expected to be present multiple times, e.g., in amplicons or fragments of different sizes. As such, reference herein to identical templates refers not only to identical template molecules but also to segments of templates that comprise the same sequence or region of interest, even if the molecules are not wholly identical.

As noted above, different characteristics possessed by different types of a given class of sequencing reaction components, e.g., in a single-molecule reaction, can affect the data collected from such a sequencing reaction. For example, different types of a particular class of nanopores, e.g. alpha hemolysin pores can have different activities, specificities, sensitivities, rates, error profiles, etc. that distinguish them from one another and also affect how they function in a sequencing reaction. In some cases, a plurality of reaction condition characteristics can be changed in combination to provide a set of varying reaction conditions in which to carry out an sequencing reaction of interest. The different reaction conditions can also include the use of different processive enzymes for controlling the rate of passage of the single stranded nucleic acid through the pore, for example different polymerases, exonucleases, or helicases as described herein.

An understanding of the characteristics of the reaction components under the set of reaction conditions used is highly beneficial during analysis of the data from the sequencing reaction(s). For example, when two nanopores with complementary characteristics are used to repeatedly sequence a single template (e.g., a single template molecule or a set of template molecules comprising overlapping or identical nucleotide sequences), the sequence reads generated by the first nanopore can be analyzed based on its known characteristics, the sequence reads generated by the second nanopore can be analyzed based on its known characteristics, and the sequence reads can be used together to construct a consensus sequence for the template, where each nucleotide position is determined based on data from both the first and second nanopore as well as their known characteristics. In some embodiments, the determination of the final consensus sequence can be carried out by combining all the individual reads together in a single operation, and in other embodiments multistep operations are used, e.g., wherein the reads from the first nanopore are used to generate a first consensus sequence, the reads from the second nanopore are used to generate a second consensus sequence, and the first and second consensus sequences are analyzed together to determine a final consensus sequence.

Further, although the present example uses reaction conditions that differ in the type of nanopore therein, other changes in reaction conditions (e.g., changes in single characteristics such as temperature, pH, divalent cation, etc., or combinations thereof) can also be used as a basis for dividing up the data and determining a set of consensus sequences to be used to derive a final consensus sequence. For example, data from sequencing reactions performed at a first pH can be used to derive a first consensus sequence and data from reactions performed at a second pH can be used to derive a second consensus sequence. In another example, the data are divided up based on multiple different reaction characteristics (e.g., pH and nanopore type) to provide a consensus sequence for each reaction condition (e.g., nanopore 1, pH1; nanopore 2, pH2; nanopore 1, pH2; and nanopore 2, pH1), which are subsequently analyzed to determine a final consensus sequence.

Yet further, different template molecules can also introduce bias into the data from a sequencing reaction. For example, different template molecules can also be associated with context-dependent error profiles. For example, template sequences having certain characteristics can cause higher incidences of specific types of errors in a sequencing read produced during passage through the nanopore. Repeatedly sequencing the template to generate redundant sequence data can provide additional information to identify such errors. Since not every read is expected to have the error, multiple sequence reads of the same template can be analyzed to identify positions that differ between the reads, thereby identifying positions having errors in some of the reads. Additional methods for generating redundant sequence information that may be used with the methods, compositions, and systems provided herein are described in U.S. Pat. No. 7,476,503 and U.S. Patent Publication No. 20090029385, which are incorporated herein by reference in their entireties for all purposes.

Another strategy is to use sequence information generated from complementary templates, since the sequence context will be different in one of the complementary templates as compared to the other. For example, a double-stranded DNA template can be denatured and each strand sequenced separately, or both strands can be in the same template molecule as described herein. The sequence information from each complementary template is analyzed based upon the raw sequence data and the known sequence context effects on the sequencing method used. Since the sequence context is different for each template, the error profiles will be different for each, and this information can be used to produce a consensus sequence for the original template. Further, sensitivity to sequence context can be modulated by changing reaction conditions. As such, multiple sequencing reactions can be performed by a single nanopores under different reaction conditions, and the resulting sequence information analyzed based upon the raw sequence data and the known reaction condition effects on the sensitivity to sequence context of the nanopore used. As will be clear to one of ordinary skill, the use of repetitive sequence information from a single-stranded template and the use of complementary sequence information from both strands of a double-stranded template can be used in combination to determine consensus sequences. In certain embodiments, single template molecules can be used to provide both repetitive and complementary sequence information, e.g., in the methods described herein in which a single molecule are passed through a nanopore multiple times.

EXAMPLES

Example 1: Repeated Sequencing and Modified Base Determination in Genomic DNA

Bacterial DNA is isolated and purified, then fragmented with sonication to produce double stranded fragments with and average length of about 5000 bases. The fragments are blunt ended, then ligated to adaptors having a single stranded restriction endonuclease site as illustrated in FIG. 11. The adaptors have palindromic regions covered by a splint as shown in FIG. 8. The primers are extended using DNA polymerase to produce a population of hemi-genomic DNA, and the extended primers are treated with single stranded restriction endonuclease to cleave at the SSRE site. The remaining oligonucleotide dissociates in the reaction medium to leave a 5' overhang of the nascent strand of 7 bases. The hemi-genomic DNA library is purified using AMPure beads.

The DNA library is added to helicase in solution under conditions where there is substantially no helicase activity, but where the helicase enzyme binds to the DNA. This mixture is added, along with the required electrolytes onto the top of a substrate having an array of MspA nanopores extending through it. A voltage is applied across the nanopore to thread the 5' ends of a DNA-helicase complex into the pores, to release the splint oligonucleotide, and form the hairpin in the strand extending through the on the nanopore. ATP and cofactors are then added to initiate helicase activity. Individual current sensors at each of the nanopores detect the current through the pore over time as the DNA molecule is translated.

After a time corresponding on average to the translation of about 1000 bases, the voltage is reversed, drawing the nascent DNA strand up into the pore. Helicase is washed from the medium, the strands are allowed to re-anneal, and fresh helicase is added. Sequencing and modified base detection are repeated as above followed again by withdrawal of the nascent strand and the addition of fresh helicase. This process is repeated 10 to 100 times. The current versus time data for the combined runs is used to determine the sequence, and the kinetics are used to identify the number and position of modified bases, e.g. methyl A in the bacterial DNA.

It is to be understood that the above description is intended to be illustrative and not restrictive. It readily should be apparent to one skilled in the art that various embodiments and—modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications, and publications are referenced. To the extent not already expressly incorporated herein, all published references and patent documents referred to in this disclosure are incorporated herein by reference in their entirety for all purposes.

What is claimed is:

1. A method for sequencing a nucleic acid and determining the presence and position of a modified base in a template nucleic acid using a nanopore comprising:
   providing a substrate having an upper solution above the substrate and a lower solution below the substrate, the substrate comprising a nanopore connecting the upper solution and lower solution, the nanopore sized to pass a single stranded nucleic acid;
   providing a voltage across the nanopore to produce a measurable current flow through the nanopore;
   providing, in the upper solution, a polymerase-nucleic acid complex comprising a strand displacing polymerase and a circular nucleic acid template which may have modified bases and providing the components required for nucleic acid synthesis, whereby the polymerase produces a nascent strand that passes through the nanopore as the nascent strand is produced;
   measuring the current through the nanopore over time as the nascent strand is translated through the nanopore;
   determining a sequence of the nascent strand as it translates through the nanopore using the measured current over time, and determining the presence of a modified base in the circular nucleic acid template using a measured change in kinetics of the polymerase, whereby the polymerase proceeds around the circular template, then continues to produce nascent strand such that a sequence in the nascent strand and the presence of a modified base in the circular template is determined more than once, and
   determining the position of the modified base using a determined value for the number of bases between the active site and the bases within the nanopore.

2. The method of claim 1 wherein the polymerase enzyme is attached to the substrate comprising the nanopore.

3. The method of claim 2 wherein the polymerase enzyme is attached proximal to the nanopore.

4. The method of claim 1 wherein the nanopore comprises a biological nanopore.

5. The method of claim 4 wherein the biological nanopore comprises an alpha hemolysin or an MspA protein.

6. The method of claim 4 wherein the polymerase is attached covalently to the biological nanopore.

7. The method of claim 1 wherein the nanopore comprises a solid state nanopore.

8. The method of claim 1 wherein the polymerase proceeds around the circular template more than twice.

9. The method of claim 1 wherein the nucleotide comprises DNA.

10. The method of claim 1 wherein the circular template comprises a double-stranded DNA portion having hairpin loops on each end of the double strand portion.

11. The method of claim 1 wherein the modified bases include methylated bases.

12. The method of claim 1 wherein the modified bases include one or more of 5-methylcytosine, N6-methyladenosine, N3-methyladenosine, N7-methylguanosine, 5-hydroxymethylcytosine, pseudouridine, thiouridine, isoguanosine, isocytosine, dihydrouridine, queuosine, wyosine, inosine, triazole, diaminopurine, β-D-glucopyranosyloxymethyluracil, 8-oxoguanosine, or 2'-O-methyl adenosine, 2'-O-methyl cytidine, 2'-O-methyl guanosine, or 2'-O-methyl uridine.

13. The method of claim 1 wherein the modified bases include 5-methylcytosine.

14. The method of claim 1 wherein the circular nucleic acid template comprises natural or genomic DNA.

15. The method of claim 1 wherein either capacitance or electron tunneling current are also measured.

16. The method of claim 1 wherein current oscillation is also measured.

17. The method of claim 1 wherein the polymerase comprises a Phi29 polymerase.

18. The method of claim 1 wherein the value for the number of bases between the active site and the bases within the nanopore is determined by sequencing and simultaneously determining kinetics of the base modification using a known sample.

19. The method of claim 1 wherein the change in kinetics results in a kinetic signature characteristic of the modified base present comprising a pattern of kinetic changes.

20. The method of claim 18 wherein the pattern of kinetic changes comprises 2, 3, 4, 6, 7, 8, or more kinetic changes.

* * * * *